(12) United States Patent
Ceccarelli et al.

(10) Patent No.: US 9,365,550 B2
(45) Date of Patent: Jun. 14, 2016

(54) BENZIMIDAZOLES AS CNS ACTIVE AGENTS

(71) Applicant: Hoffmann-La Roche Inc., Little Falls, NJ (US)

(72) Inventors: Simona M. Ceccarelli, Basel (CH); Ravi Jagasia, Loerrach (DE); Roland Jakob-Roetne, Inzlingen (DE); Juergen Wichmann, Steinen (DE)

(73) Assignee: Hoffmann-La Roche Inc., Little Falls, NJ (US)

( * ) Notice: Subject to any disclaimer, the term of this patent is extended or adjusted under 35 U.S.C. 154(b) by 0 days.

(21) Appl. No.: 14/675,404

(22) Filed: Mar. 31, 2015

(65) Prior Publication Data
US 2015/0203472 A1 Jul. 23, 2015

Related U.S. Application Data

(63) Continuation of application No. PCT/EP2013/070166, filed on Sep. 27, 2013.

(30) Foreign Application Priority Data

Oct. 1, 2012 (EP) .................................... 12186784

(51) Int. Cl.
*A61K 31/44* (2006.01)
*C07D 403/04* (2006.01)
*C07D 401/14* (2006.01)

(52) U.S. Cl.
CPC ............ *C07D 403/04* (2013.01); *C07D 401/14* (2013.01)

(58) Field of Classification Search
None
See application file for complete search history.

(56) References Cited

U.S. PATENT DOCUMENTS 7,074,801 B1 * 7/2006 Yoshida et al. .......... 514/266.23

FOREIGN PATENT DOCUMENTS

WO 2008/046072 A2 4/2008
WO 2008016123 7/2008
WO 2012/006419 A2 1/2012

OTHER PUBLICATIONS

Ransome M et al Neuroplasticity vol. 2012 pp. 1-7.*
Ming, G-l et al Neuron vol. 70 2011, pp. 687-702.*
Sahay, A. et al., Neuron vol. 70 2011 pp. 582-588.*
Izumikawa, M et al ature Medicine 2005 vol. 11 pp. 271-276.*
ISR for PCT/EP2013/070116.
Japanese Laid-open Patent [Kokai] Publication No. 2008-533162.
Japanese Laid-open Patent [Kokai] Publication No. 2009-521516.
Japanese Laid-open Patent [Kokai] Publication No. 2009-530353.
Japanese Laid-open Patent [Kokai] Publication No. 2012-520238.
Japanese Laid-open Patent [Kokai] Publication No. Hei 11-501320.

* cited by examiner

Primary Examiner — Heidi Reese

(57) ABSTRACT

The present invention relates to compounds of general formula

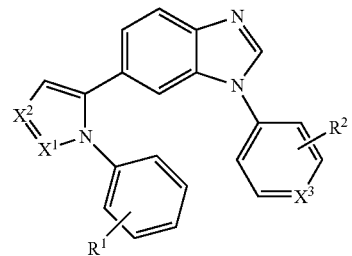

wherein
$R^1$ hydrogen, lower alkyl, halogen or lower alkyl substituted by halogen;
$R^2$ is hydrogen or halogen;
$X^1$ is N or CH;
$X^2$ is N or CH;
with the proviso that only one of $X^1$ or $X^2$ is N;
$X^3$ is C(R) or N;
and R is hydrogen, lower alkyl, halogen, lower alkyl substituted by halogen, lower alkoxy or $SO_2$-lower alkyl;
or to a pharmaceutically acceptable acid addition salt, to a racemic mixture or to its corresponding enantiomer and/or optical isomers thereof.
The compounds may be used for the treatment of schizophrenia, obsessive-compulsive personality disorder, major depression, bipolar disorders, anxiety disorders, normal aging, epilepsy, retinal degeneration, traumatic brain injury, spinal cord injury, post-traumatic stress disorder, panic disorder, Parkinson's disease, dementia, Alzheimer's disease, mild cognitive impairment, chemotherapy-induced cognitive dysfunction, Down syndrome, autism spectrum disorders, hearing loss, tinnitus, spinocerebellar ataxia, amyotrophic lateral sclerosis, multiple sclerosis, Huntington's disease, stroke, radiation therapy, chronic stress, abuse of neuro-active drugs, such as alcohol, opiates, methamphetamine, phencyclidine and cocaine.

13 Claims, No Drawings

BENZIMIDAZOLES AS CNS ACTIVE AGENTS

The present invention relates to compounds of general formula

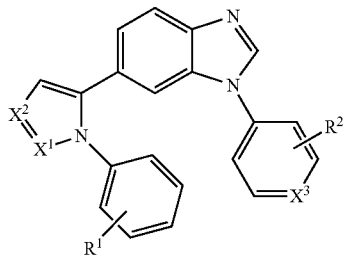

wherein
$R^1$ hydrogen, lower alkyl, halogen or lower alkyl substituted by halogen;
$R^2$ is hydrogen or halogen;
$X^1$ is N or CH;
$X^2$ is N or CH;
  with the proviso that only one of $X^1$ or $X^2$ is N;
$X^3$ is C(R) or N;
  and R is hydrogen, lower alkyl, halogen, lower alkyl substituted by halogen, lower alkoxy or $SO_2$-lower alkyl;
or to a pharmaceutically acceptable acid addition salt, to a racemic mixture or to its corresponding enantiomer and/or optical isomers thereof.

Now it has been shown that the present compounds stimulate neurogenesis from neural stem cells (NSCs). Neurogenesis occurs in the developing and adult brain. Conceptually, this process of neurogenesis can be divided into four steps: (i) proliferation of NSCs; (ii) neuronal fate determination of NSC; (iii) survival and maturation of new neurons; and (iv) functional integration of new neurons into the neuronal network.

Adult neurogenesis is a developmental process that occurs throughout live in the adult brain whereby new functional neurons are generated from adult neural stem cells. Constitutive adult neurogenesis under physiological conditions occurs mainly in two "neurogenic" brain regions, 1) the sub-granular zone (SGZ) in the dentate gyrus of the hippocampus, where new dentate granule cells are generated, 2) the sub-ventricular zone (SVZ) of the lateral ventricles, where new neurons are generated and then migrate through the rostral migratory stream (RMS) to the olfactory bulb to become interneurons.

Extensive evidence suggests that hippocampal adult neurogenesis plays an important role in cognitive and emotional states albeit the precise function remains elusive. It has been argued that the relatively small number of newborn granule neurons can affect global brain function because they innervate many interneurons within the dentate gyrus, each of which inhibits hundreds of mature granule cells leading to a neurogenesis-dependent feedback inhibition. In combination with a low threshold for firing the newborn neurons trigger responses to very subtle changes in context. Disturbances in this process may manifest behaviorally in deficits in pattern separation related to psychiatric diseases. For example, adult hippocampal neurogenesis correlates with cognitive and emotional capacity, e.g. physical exercise, exposure to an enriched environment and typical antidepressants concomitantly promote adult hippocampal neurogenesis and cognition and/or emotional states, while chronic stress, depression, sleep deprivation and aging decrease adult neurogenesis and associate with negative cognitive and/or emotional states (Neuron 70, May 26, 2011, pp 582-588 and pp 687-702; WO 2008/046072). Interestingly, antidepressants promote hippocampal adult neurogenesis and their effects on certain behaviors require the stimulation of neurogenesis. Neurogenesis in other adult CNS regions is generally believed to be very limited under normal physiological conditions, but could be induced after injury such as stroke, and central and peripheral brain damage.

It is therefore believed that stimulation of adult neurogenesis represents a neuroregenerative therapeutic target for normal aging and in particular for a variety of neurodegenerative and neuropsychiatric diseases, including schizophrenia, obsessive-compulsive personality disorder, major depression, bipolar disorders, anxiety disorders, epilepsy, retinal degeneration, traumatic brain injury, spinal cord injury, post-traumatic stress disorder, panic disorder, Parkinson's disease, dementia, Alzheimer's disease, mild cognitive impairment, chemotherapy-induced cognitive dysfunction ("chemobrain"), Down syndrome, autism spectrum disorders, hearing loss (Neuroscience, 167 (2010) 1216-1226; Nature Medicine, Vol. 11, number 3, (2005), 271-276) tinnitus, spinocerebellar ataxia, amyotrophic lateral sclerosis, multiple sclerosis, Huntington's disease, stroke, and disturbances due to radiation therapy, chronic stress, or abuse of neuro-active drugs, such as alcohol, opiates, methamphetamine, phencyclidine and cocaine (US 2012/0022096).

Hence, chemical stimulation of adult neurogenesis offers new regenerative avenues and opportunities to develop novel drugs for treating neurological diseases and neuropsychiatric disorders.

Therefore, the object of the present invention was to identify compounds that modulate neurogenesis. It has been found that the compounds of formula I are active in this area and they may therefore be used for the treatment of schizophrenia, obsessive-compulsive personality disorder, major depression, bipolar disorders, anxiety disorders, normal aging, epilepsy, retinal degeneration, traumatic brain injury, spinal cord injury, post-traumatic stress disorder, panic disorder, Parkinson's disease, dementia, Alzheimer's disease, mild cognitive impairment, chemotherapy-induced cognitive dysfunction ("chemobrain"), Down syndrome, autism spectrum disorders, hearing loss, tinnitus, spinocerebellar ataxia, amyotrophic lateral sclerosis, multiple sclerosis, Huntington's disease, stroke, and disturbances due to radiation therapy, chronic stress, or abuse of neuro-active drugs, such as alcohol, opiates, methamphetamine, phencyclidine and cocaine.

The most preferred indications for compounds of formula I are Alzheimer's disease, depression, anxiety disorders and stroke.

The present invention relates to compounds of formula I and to their pharmaceutically acceptable salts, in cases where this applies to mixtures of enantiomers or diastereomers or their enantiomerically or diastereomerically pure forms, to these compounds as pharmaceutically active substances, to the processes for their production, as well as to the use in the treatment or prevention of disorders, relating to neurogenesis, schizophrenia, obsessive-compulsive personality disorder, major depression, bipolar disorders, anxiety disorders, normal aging, epilepsy, retinal degeneration, traumatic brain injury, spinal cord injury, post-traumatic stress disorder, Parkinson's disease, dementia, Alzheimer's disease, mild cognitive impairment, chemotherapy-induced cognitive dysfunction, Down syndrome, autism spectrum disorders, hearing loss, tinnitus, spinocerebellar ataxia, amyotrophic lateral sclerosis, multiple sclerosis, Huntington's disease, stroke, radiation therapy, chronic stress, abuse of neuro-active drugs, such as alcohol, opiates, methamphetamine, phencyclidine and cocaine, and to pharmaceutical compositions containing the compounds of formula I.

The following definitions of the general terms used in the present description apply irrespective of whether the terms in question appear alone or in combination.

As used herein, the term "lower alkyl" denotes a saturated, i.e. aliphatic hydrocarbon group including a straight or branched carbon chain with 1-4 carbon atoms. Examples for "alkyl" are methyl, ethyl, n-propyl, and isopropyl.

The term "lower alkoxy" denotes a group O—R' wherein R' is lower alkyl as defined above.

The term "lower alkyl substituted by halogen" denotes a lower alkyl group as defined above and wherein at least one hydrogen atom is replaced by halogen.

The term "halogen" denotes chlorine, bromine, fluorine or iodine.

The term "pharmaceutically acceptable salt" or "pharmaceutically acceptable acid addition salt" embraces salts with inorganic and organic acids, such as hydrochloric acid, nitric acid, sulfuric acid, phosphoric acid, citric acid, formic acid, fumaric acid, maleic acid, acetic acid, succinic acid, tartaric acid, methane-sulfonic acid, p-toluenesulfonic acid and the like.

One embodiment of the invention are compounds of formula

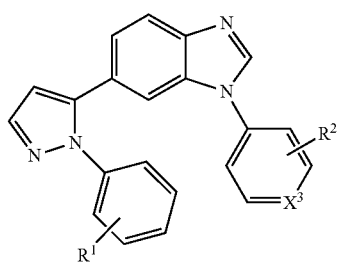

IA wherein
$R^1$ hydrogen, lower alkyl, halogen or lower alkyl substituted by halogen;
$R^2$ is hydrogen or halogen;
$X^3$ is C(R) or N;
and R is hydrogen, lower alkyl, halogen, lower alkyl substituted by halogen, lower alkoxy or $SO_2$-lower alkyl;
or a pharmaceutically acceptable acid addition salt, a racemic mixture or its corresponding enantiomer and/or optical isomers thereof, for example 1-p-Tolyl-6-(2-p-tolyl-2H-pyrazol-3-yl)-1H-benzoimidazole
1-Phenyl-6-(2-phenyl-2H-pyrazol-3-yl)-1H-benzoimidazole
6-[2-(4-Fluoro-phenyl)-2H-pyrazol-3-yl]-1-phenyl-1H-benzoimidazole
1-Phenyl-6-(2-p-tolyl-2H-pyrazol-3-yl)-1H-benzoimidazole
6-(2-Phenyl-2H-pyrazol-3-yl)-1-p-tolyl-1H-benzoimidazole
6-[2-(4-Fluoro-phenyl)-2H-pyrazol-3-yl]-1-p-tolyl-1H-benzoimidazole
1-(4-Fluoro-phenyl)-6-(2-phenyl-2H-pyrazol-3-yl)-1H-benzoimidazole
1-(4-Fluoro-phenyl)-6-[2-(4-fluoro-phenyl)-2H-pyrazol-3-yl]-1H-benzoimidazole
1-(4-Fluoro-phenyl)-6-(2-p-tolyl-2H-pyrazol-3-yl)-1H-benzoimidazole
1-(4-Fluoro-phenyl)-6-[2-(4-trifluoromethyl-phenyl)-2H-pyrazol-3-yl]-1H-benzoimidazole
6-[2-(4-Chloro-phenyl)-2H-pyrazol-3-yl]-1-(4-fluoro-phenyl)-1H-benzoimidazole
1-(4-Chloro-phenyl)-6-[2-(4-trifluoromethyl-phenyl)-2H-pyrazol-3-yl]-1H-benzoimidazole
1-(4-Chloro-phenyl)-6-[2-(4-chloro-phenyl)-2H-pyrazol-3-yl]-1H-benzoimidazole
6-[2-(4-Chloro-phenyl)-2H-pyrazol-3-yl]-1-(4-trifluoromethyl-phenyl)-1H-benzoimidazole
1-(2,4-Difluoro-phenyl)-6-[2-(4-trifluoromethyl-phenyl)-2H-pyrazol-3-yl]-1H-benzoimidazole
6-[2-(4-Chloro-phenyl)-2H-pyrazol-3-yl]-1-(2,4-difluoro-phenyl)-1H-benzoimidazole
1-(2,4-Difluoro-phenyl)-6-[2-(4-fluoro-phenyl)-2H-pyrazol-3-yl]-1H-benzoimidazole
6-[2-(4-Fluoro-phenyl)-2H-pyrazol-3-yl]-1-(4-trifluoromethyl-phenyl)-1H-benzoimidazole
1-(4-Chloro-phenyl)-6-[2-(4-fluoro-phenyl)-2H-pyrazol-3-yl]-1H-benzoimidazole
6-[2-(4-Fluoro-phenyl)-2H-pyrazol-3-yl]-1-pyridin-4-yl-1H-benzoimidazole
6-[2-(4-Chloro-phenyl)-2H-pyrazol-3-yl]-1-pyridin-4-yl-1H-benzoimidazole
1-(4-Chloro-2-fluoro-phenyl)-6-[2-(4-fluoro-phenyl)-2H-pyrazol-3-yl]-1H-benzoimidazole
1-(4-Chloro-2-fluoro-phenyl)-6-[2-(4-chloro-phenyl)-2H-pyrazol-3-yl]-1H-benzoimidazole
6-[2-(4-Fluoro-phenyl)-2H-pyrazol-3-yl]-1-(4-methoxy-phenyl)-1H-benzoimidazole
6-[2-(4-Chloro-phenyl)-2H-pyrazol-3-yl]-1-(4-methoxy-phenyl)-1H-benzoimidazole
6-[2-(4-Fluoro-phenyl)-2H-pyrazol-3-yl]-1-(4-methane-sulfonyl-phenyl)-1H-benzoimidazole or
6-[2-(4-Chloro-phenyl)-2H-pyrazol-3-yl]-1-(4-methane-sulfonyl-phenyl)-1H-benzoimidazole.

One further embodiment of the invention are compounds of formula

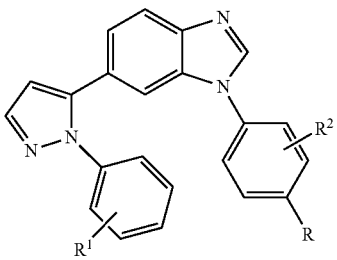

IA-1 wherein
$R^1$ hydrogen, lower alkyl, halogen or lower alkyl substituted by halogen;
$R^2$ is hydrogen or halogen;
R is hydrogen, lower alkyl, halogen, lower alkyl substituted by halogen, lower alkoxy or $SO_2$-lower alkyl;
or a pharmaceutically acceptable acid addition salt, a racemic mixture or its corresponding enantiomer and/or optical isomers thereof, for example 1-p-Tolyl-6-(2-p-tolyl-2H-pyrazol-3-yl)-1H-benzoimidazole
1-Phenyl-6-(2-phenyl-2H-pyrazol-3-yl)-1H-benzoimidazole
6-[2-(4-Fluoro-phenyl)-2H-pyrazol-3-yl]-1-phenyl-1H-benzoimidazole 1-Phenyl-6-(2-p-tolyl-2H-pyrazol-3-yl)-1H-benzoimidazole
6-(2-Phenyl-2H-pyrazol-3-yl)-1-p-tolyl-1H-benzoimidazole
6-[2-(4-Fluoro-phenyl)-2H-pyrazol-3-yl]-1-p-tolyl-1H-benzoimidazole
1-(4-Fluoro-phenyl)-6-(2-phenyl-2H-pyrazol-3-yl)-1H-benzoimidazole
1-(4-Fluoro-phenyl)-6-[2-(4-fluoro-phenyl)-2H-pyrazol-3-yl]-1H-benzoimidazole
1-(4-Fluoro-phenyl)-6-(2-p-tolyl-2H-pyrazol-3-yl)-1H-benzoimidazole
1-(4-Fluoro-phenyl)-6-[2-(4-trifluoromethyl-phenyl)-2H-pyrazol-3-yl]-1H-benzoimidazole
6-[2-(4-Chloro-phenyl)-2H-pyrazol-3-yl]-1-(4-fluoro-phenyl)-1H-benzoimidazole
1-(4-Chloro-phenyl)-6-[2-(4-trifluoromethyl-phenyl)-2H-pyrazol-3-yl]-1H-benzoimidazole
1-(4-Chloro-phenyl)-6-[2-(4-chloro-phenyl)-2H-pyrazol-3-yl]-1H-benzoimidazole
6-[2-(4-Chloro-phenyl)-2H-pyrazol-3-yl]-1-(4-trifluoromethyl-phenyl)-1H-benzoimidazole
1-(2,4-Difluoro-phenyl)-6-[2-(4-trifluoromethyl-phenyl)-2H-pyrazol-3-yl]-1H-benzoimidazole
6-[2-(4-Chloro-phenyl)-2H-pyrazol-3-yl]-1-(2,4-difluoro-phenyl)-1H-benzoimidazole
1-(2,4-Difluoro-phenyl)-6-[2-(4-fluoro-phenyl)-2H-pyrazol-3-yl]-1H-benzoimidazole
6-[2-(4-Fluoro-phenyl)-2H-pyrazol-3-yl]-1-(4-trifluoromethyl-phenyl)-1H-benzoimidazole
1-(4-Chloro-phenyl)-6-[2-(4-fluoro-phenyl)-2H-pyrazol-3-yl]-1H-benzoimidazole
1-(4-Chloro-2-fluoro-phenyl)-6-[2-(4-fluoro-phenyl)-2H-pyrazol-3-yl]-1H-benzoimidazole
1-(4-Chloro-2-fluoro-phenyl)-6-[2-(4-chloro-phenyl)-2H-pyrazol-3-yl]-1H-benzoimidazole
6-[2-(4-Fluoro-phenyl)-2H-pyrazol-3-yl]-1-(4-methoxy-phenyl)-1H-benzoimidazole
6-[2-(4-Chloro-phenyl)-2H-pyrazol-3-yl]-1-(4-methoxy-phenyl)-1H-benzoimidazole
6-[2-(4-Fluoro-phenyl)-2H-pyrazol-3-yl]-1-(4-methane-sulfonyl-phenyl)-1H-benzoimidazole or
6-[2-(4-Chloro-phenyl)-2H-pyrazol-3-yl]-1-(4-methane-sulfonyl-phenyl)-1H-benzoimidazole.

One further embodiment of the invention are compounds of formula

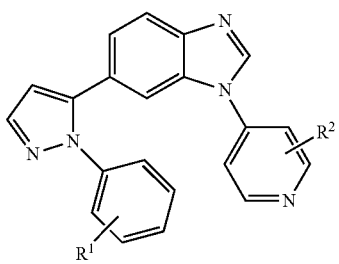

IA-2 wherein
R¹ hydrogen, lower alkyl, halogen or lower alkyl substituted by halogen;
R² is hydrogen or halogen;
or a pharmaceutically acceptable acid addition salt, a racemic mixture or its corresponding enantiomer and/or optical isomers thereof, for example
6-[2-(4-Fluoro-phenyl)-2H-pyrazol-3-yl]-1-pyridin-4-yl-1H-benzoimidazole or
6-[2-(4-Chloro-phenyl)-2H-pyrazol-3-yl]-1-pyridin-4-yl-1H-benzoimidazole.

One further embodiment of the invention are compounds of formula

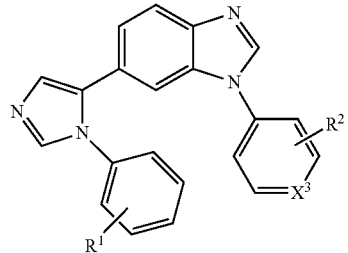

IB wherein
R¹ hydrogen, lower alkyl, halogen or lower alkyl substituted by halogen;
R² is hydrogen or halogen;
X³ is C(R) or N;
and R is hydrogen, lower alkyl, halogen, lower alkyl substituted by halogen, lower alkoxy or $SO_2$-lower alkyl;
or a pharmaceutically acceptable acid addition salt, a racemic mixture or its corresponding enantiomer and/or optical isomers thereof, for example
1-(4-Fluoro-phenyl)-6-(3-phenyl-3H-imidazol-4-yl)-1H-benzoimidazole
6-[3-(4-Chloro-phenyl)-3H-imidazol-4-yl]-1-(4-fluoro-phenyl)-1H-benzoimidazole or
1-(4-Fluoro-phenyl)-6-[3-(4-fluoro-phenyl)-3H-imidazol-4-yl]-1H-benzoimidazole.

The present compounds of formula I and their pharmaceutically acceptable salts can be prepared by methods known in the art, for example, by processes described below, which process comprises
reacting a compound of formula

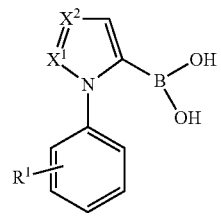

1 with a compound of formula

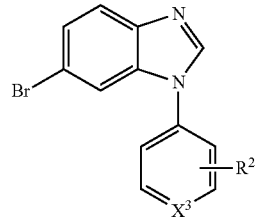

2 to a compound of formula

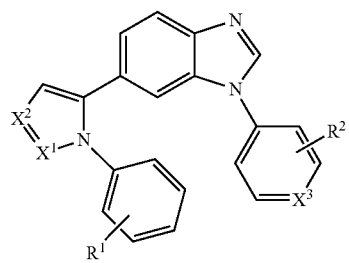

I and, if desired, converting the compounds obtained into pharmaceutically acceptable acid addition salts.

The preparation of compounds of formula I of the present invention may be carried out in sequential or convergent synthetic routes. Syntheses of the compounds of the invention are shown in the following scheme 1. The skills required for carrying out the reaction and purification of the resulting products are known to those skilled in the art. The substituents and indices used in the following description of the processes have the significance given herein before unless indicated to the contrary.

In more detail, the compounds of formula I can be manufactured by the methods given below, by the methods given in the examples or by analogous methods. Appropriate reaction conditions for the individual reaction steps are known to a person skilled in the art. The reaction sequence is not limited to the one displayed in scheme 1, however, depending on the starting materials and their respective reactivity the sequence of reaction steps can be freely altered. Starting materials are either commercially available or can be prepared by methods analogous to the methods given below, by methods described in references cited in the description or in the examples, or by methods known in the art.

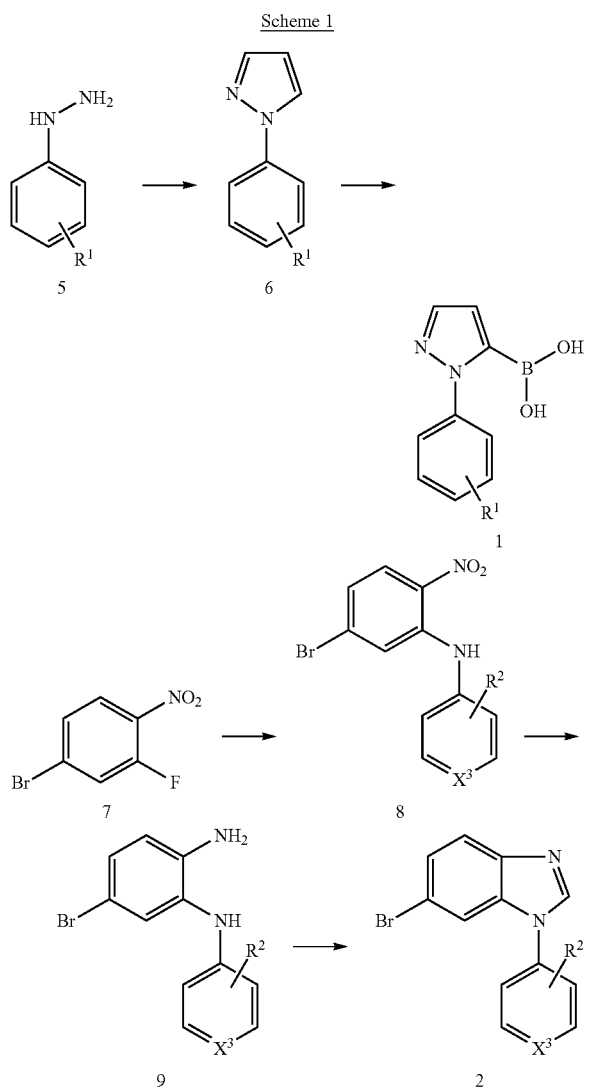

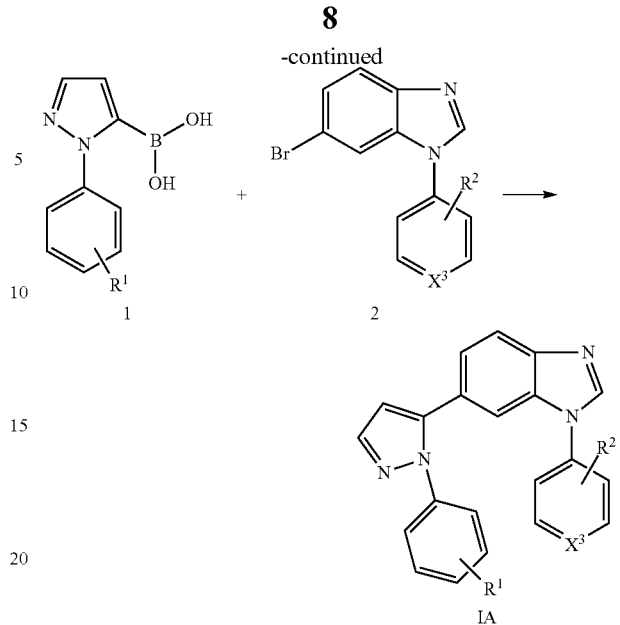

The compounds of formula IA can be prepared by the palladium catalyzed coupling reaction of bromo-benzimidazoles 2 and boronic acids 1 (scheme I).

The boronic acids 1 are either commercially available or can be prepared from the corresponding phenyl-imidazoles 6 by treatment with n-butyllithium and triisopropyl borate at −78° C. If not commercially available, the phenyl-imidazoles 6 can be prepared from the corresponding phenyl-hydrazines 5.

The bromo-benzimidazoles 2 can be prepared by reacting 4-bromo-2-fluoro-nitrobenzene 7 with the corresponding anilines 8 followed by reduction of the nitro-group to the 1,2-diamino-benzene derivatives 9, which are subsequently transformed into the benzimidazoles 2 by treatment with trimethyl orthoformiate and formic acid.

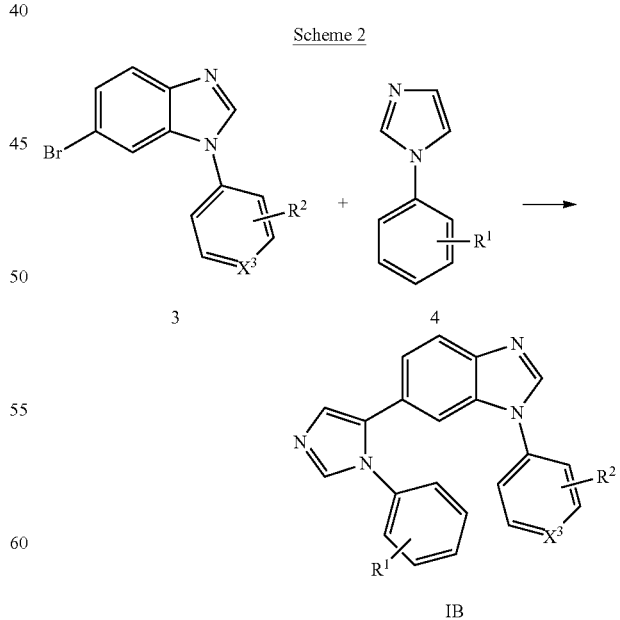

The related imidazole derivatives of formula IB can easily be prepared by palladium catalyzed coupling reaction of the bromo-benzimidazoles 3 with commercially available phenyl-imidazoles 4 (scheme 2).

Isolation and Purification of the Compounds

Isolation and purification of the compounds and intermediates described herein can be effected, if desired, by any suitable separation or purification procedure such as, for example, filtration, extraction, crystallization, column chromatography, thin-layer chromatography, thick-layer chromatography, preparative low or high-pressure liquid chromatography or a combination of these procedures. Specific illustrations of suitable separation and isolation procedures can be had by reference to the preparations and examples herein below. However, other equivalent separation or isolation procedures could, of course, also be used. Racemic mixtures of chiral compounds of formula I can be separated using chiral HPLC.

Salts of Compounds of Formula I

The compounds of formula I are basic and may be converted to a corresponding acid addition salt. The conversion is accomplished by treatment with at least a stoichiometric amount of an appropriate acid, such as hydrochloric acid, hydrobromic acid, sulfuric acid, nitric acid, phosphoric acid and the like, and organic acids such as acetic acid, propionic acid, glycolic acid, pyruvic acid, oxalic acid, malic acid, malonic acid, succinic acid, maleic acid, fumaric acid, tartaric acid, citric acid, benzoic acid, cinnamic acid, mandelic acid, methanesulfonic acid, ethanesulfonic acid, p-toluenesulfonic acid, salicylic acid and the like. Typically, the free base is dissolved in an inert organic solvent such as diethyl ether, ethyl acetate, chloroform, ethanol or methanol and the like, and the acid added in a similar solvent. The temperature is maintained between 0° C. and 50° C. The resulting salt precipitates spontaneously or may be brought out of solution with a less polar solvent.

The acid addition salts of the basic compounds of formula I may be converted to the corresponding free bases by treatment with at least a stoichiometric equivalent of a suitable base such as sodium or potassium hydroxide, potassium carbonate, sodium bicarbonate, ammonia, and the like.

The compounds of formula I and their pharmaceutically usable addition salts possess valuable pharmacological properties. Specifically, it has been found that the compounds of the present invention have an activity as neurogenic agents.

The compounds were investigated in accordance with the test given hereinafter.

Neurogenesis Assay

Neural Stem Cell Proliferation Assay

Neurogenic properties of small molecules are determined based on the proliferation of human embryonic stem cell derived neural stem cells (NSCs) which were derived via a dual smad inhibition as previously described (Chambers, S. M., et al., *Highly efficient neural conversion of human ES and iPS cells by dual inhibition of SMAD signaling*, Nature biotechnology, 2009. 27(3): p. 275-80.)

Compounds respond is measured by the increase in cells based on ATP levels (Promega:CellTiterGlo®) after an incubation period of 4 days.

NSCs are thawed and expanded over 3 passages. On the 14$^{th}$ day, NSCs are seeded in Polyornithin/Laminin coated 384 well plates at a cell density of 21,000 cells/cm$^2$ in a media volume of 38 µL.

4 hours after cell seeding, compound solutions are added at a volume of 2 µl. Stock solutions of the compounds (water, 5% DMSO) are diluted to obtain a dose response (11 points, dilution factor is 2), ranging from 8 µM to 8 nM. Controls are run to consistently determine the neurogenic properties of the cells:

Negative (neutral) control is cell culture Media (final DMSO concentration: 0.25%).

Positive controls are:
1. cell culture Media+100 ng/ml FGF2 (final DMSO concentration: 0.1%)
2. cell culture Media+20 ng/ml EGF (final DMSO concentration: 0.1%)
3. cell culture Media+100 ng/ml Wnt3a (final DMSO concentration: 0.1%)

After 4 days incubation at 37° C., 5% $CO_2$, the amount of ATP per well is quantified. The ATP concentration is proportional to the cell number. ATP is quantified by using the Promega CellTiterGlo® kit. The CellTiterGlo® reagents contain a cell lysis buffer, a thermo stable luciferase (Ultra-Glo™ recombinant luciferase), magnesium and luciferin. Luciferin reacts with ATP producing oxyluciferin, AMP and light. The luminescence signal is proportional to the ATP content.

The value of negative (neutral) control is determined for each assay plate by taking the average of 16 negative control wells. The neurogenic compound response is calculated for each compound as (compound/Negative Control)*100.

The values of $EC_{150}$ from the dose response curve are determined for each test compound. The $EC_{150}$ is the compound concentration at which 150% activity of control (100%) is reached. The preferred compounds show a $EC_{150}$ (µM) in the range of <2.8 µM as shown in the table below.

List of Examples and $EC_{150}$ Data

| Ex. | Structure | Name | $EC_{150}$ (uM) |
|---|---|---|---|
| 1 | 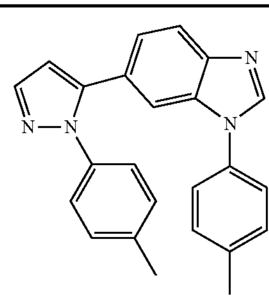 | 1-p-Tolyl-6-(2-p-tolyl-2H-pyrazol-3-yl)-1H-benzoimidazole | 0.008 |
| 2 | 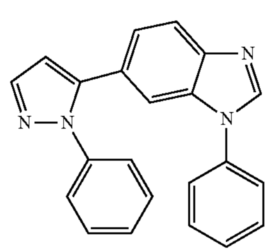 [SMILES: c1ccc(-n2nccc2-c2ccc3ncn(-c4ccccc4)c3c2)cc1] | 1-Phenyl-6-(2-phenyl-2H-pyrazol-3-yl)-1H-benzoimidazole | 0.014 |

| Ex. | Structure | Name | EC$_{150}$ (uM) |
|---|---|---|---|
| 3 | 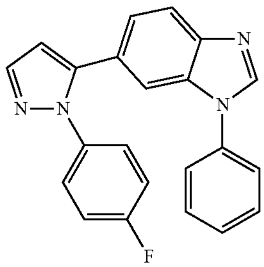 [SMILES: Fc1ccc(-n2nccc2-c2ccc3ncn(-c4ccccc4)c3c2)cc1] | 6-[2-(4-Fluoro-phenyl)-2H-pyrazol-3-yl]-1-phenyl-1H-benzoimidazole | 0.024 |
| 4 | 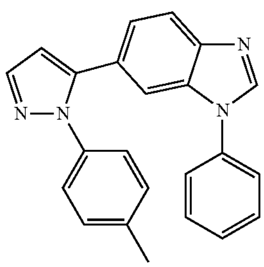 [SMILES: Cc1ccc(-n2nccc2-c2ccc3ncn(-c4ccccc4)c3c2)cc1] | 1-Phenyl-6-(2-p-tolyl-2H-pyrazol-3-yl)-1H-benzoimidazole | 0.015 |
| 5 | 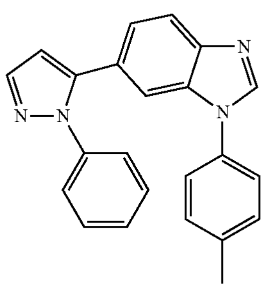 [SMILES: Cc1ccc(-n2cnc3ccc(-c4ccnn4-c4ccccc4)cc32)cc1] | 6-(2-Phenyl-2H-pyrazol-3-yl)-1-p-tolyl-1H-benzoimidazole | 0.0165 |
| 6 | 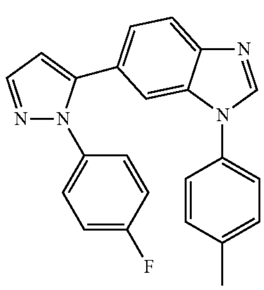 | 6-[2-(4-Fluoro-phenyl)-2H-pyrazol-3-yl]-1-p-tolyl-1H-benzoimidazle | 0.0195 |
| 7 | 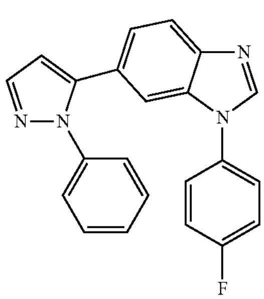 [SMILES: Fc1ccc(-n2cnc3ccc(-c4ccnn4-c4ccccc4)cc32)cc1] | 1-(4-Fluoro-phenyl)-6-(2-phenyl-2H-pyrazol-3-yl)-1H-benzoimidazole | 0.031 |

| Ex. | Structure | Name | EC$_{150}$ (uM) |
|---|---|---|---|
| 8 | 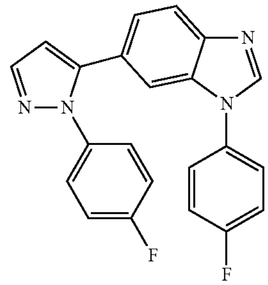 | 1-(4-Fluoro-phenyl)-6-[2-(4-fluoro-phenyl)-2H-pyrazol-3-yl]-1H-benzoimidazole | 0.044 |
| 9 | 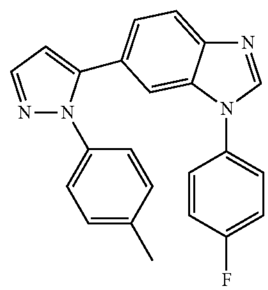 | 1-(4-Fluoro-phenyl)-6-(2-p-tolyl-2H-pyrazol-3-yl)-1H-benzoimidazole | 0.009 |
| 10 | 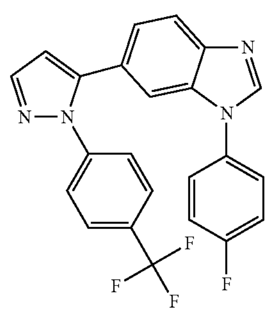 [SMILES: Fc1ccc(-n2cnc3ccc(-c4ccnn4-c4ccc(C(F)(F)F)cc4)cc32)cc1] | 1-(4-Fluoro-phenyl)-6-[2-(4-trifluoromethyl-phenyl)-2H-pyrazol-3-yl]-1H-benzoimidazole | 1.1 |
| 11 | 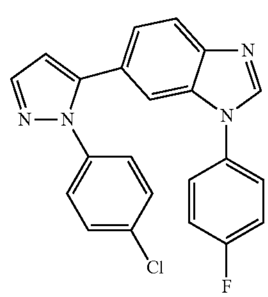 [SMILES: Fc1ccc(-n2cnc3ccc(-c4ccnn4-c4ccc(Cl)cc4)cc32)cc1] | 6-[2-(4-Chloro-phenyl)-2H-pyrazol-3-yl]-1-(4-fluoro-phenyl)-1H-benzoimidazole | 0.11 |
| 12 | 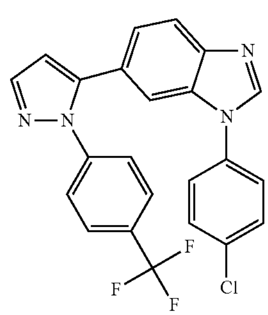 | 1-(4-Chloro-phenyl)-6-[2-(4-trifluoromethyl-phenyl)-2H-pyrazol-3-yl]-1H-benzoimidazole | 0.71 |

-continued

| Ex. | Structure | Name | EC$_{150}$ (uM) |
|---|---|---|---|
| 13 | 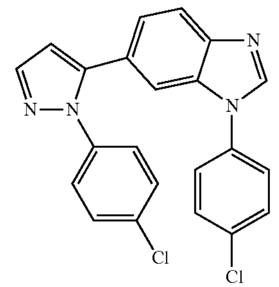 [SMILES: Clc1ccc(-n2nccc2-c2ccc3ncn(-c4ccc(Cl)cc4)c3c2)cc1] | 1-(4-Chloro-phenyl)-6-[2-(4-chloro-phenyl)-2H-pyrazol-3-yl]-1H-benzoimidazole | 0.082 |
| 14 | 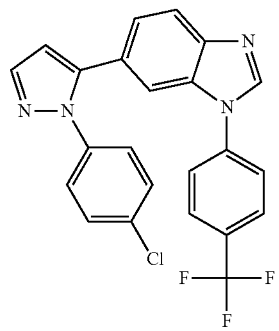 | 6-[2-(4-Chloro-phenyl)-2H-pyrazol-3-yl]-1-(4-trifluoromethyl-phenyl)-1H-benzoimidazole | 0.62 |
| 15 | 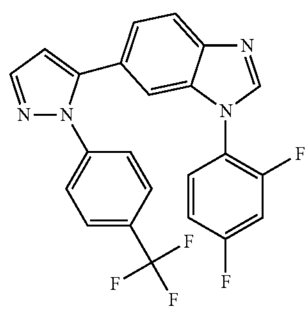 [SMILES: Fc1ccc(-n2cnc3ccc(-c4ccnn4-c4ccc(C(F)(F)F)cc4)cc32)c(F)c1] | 1-(2,4-Difluoro-phenyl)-6-[2-(4-trifluoromethyl-phenyl)-2H-pyrazol-3-yl]-1H-benzoimidazole | 1.33 |
| 16 | 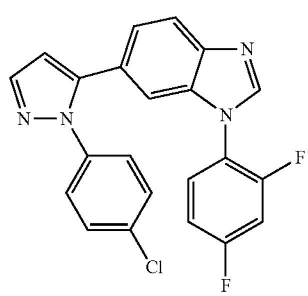 | 6-[2-(4-Chloro-phenyl)-2H-pyrazol-3-yl]-1-(2,4-difluoro-phenyl)-1H-benzoimidazole | 0.19 |
| 17 | 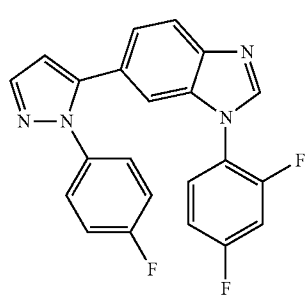 | 1-(2,4-Difluoro-phenyl)-6-[2-(4-fluoro-phenyl)-2H-pyrazol-3-yl]-1H-benzoimidazole | 0.047 |

-continued

| Ex. | Structure | Name | EC$_{150}$ (uM) |
|---|---|---|---|
| 18 | 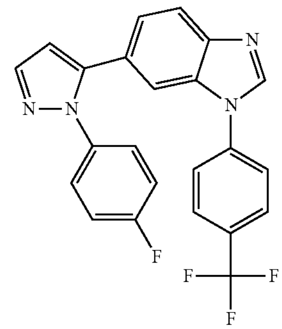 | 6-[2-(4-Fluoro-phenyl)-2H-pyrazol-3-yl]-1-(4-trifluoromethyl-phenyl)-1H-benzoimidazole | 0.41 |
| 19 | 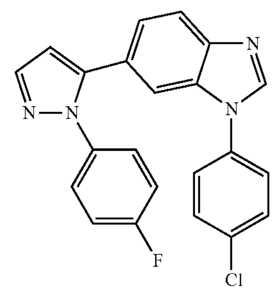 | 1-(4-Chloro-phenyl)-6-[2-(4-fluoro-phenyl)-2H-pyrazol-3-yl]-1H-benzoimidazole | 0.09 |
| 20 | 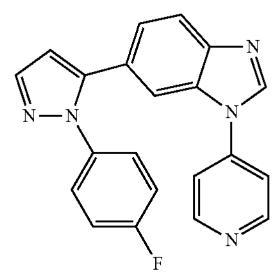 [SMILES: Fc1ccc(-n2nccc2-c2ccc3ncn(-c4ccncc4)c3c2)cc1] | 6-[2-(4-Fluoro-phenyl)-2H-pyrazol-3-yl]-1-pyridin-4-yl-1H-benzoimidazole | 0.044 |
| 21 | 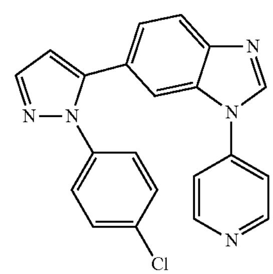 [SMILES: Clc1ccc(-n2nccc2-c2ccc3ncn(-c4ccncc4)c3c2)cc1] | 6-[2-(4-Chloro-phenyl)-2H-pyrazol-3-yl]-1-pyridin-4-yl-1H-benzoimidazole | 0.036 |
| 22 | 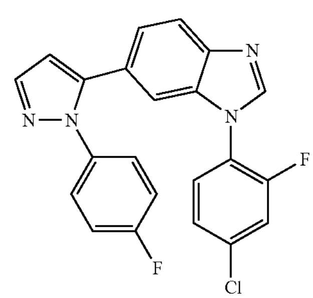 | 1-(4-Chloro-2-fluoro-phenyl)-6-[2-(4-fluoro-phenyl)-2H-pyrazol-3-yl]-1H-benzoimidazole | 0.084 |

| Ex. | Structure | Name | EC$_{150}$ (uM) |
|---|---|---|---|
| 23 | 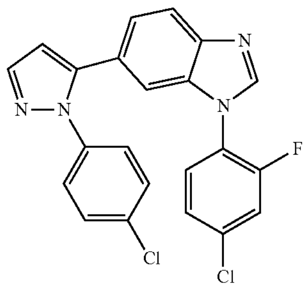 | 1-(4-Chloro-2-fluoro-phenyl)-6-[2-(4-chloro-phenyl)-2H-pyrazol-3-yl]-1H-benzoimidazole | 0.17 |
| 24 | 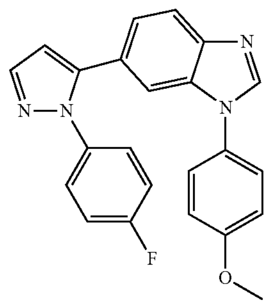 | 6-[2-(4-Fluoro-phenyl)-2H-pyrazol-3-yl]-1-(4-methoxy-phenyl)-1H-benzoimidazole | 0.021 |
| 25 | 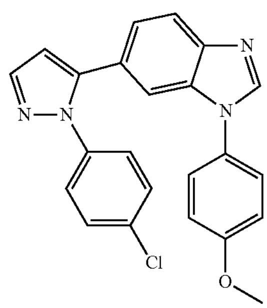 [SMILES: COc1ccc(-n2cnc3ccc(-c4ccnn4-c4ccc(F)cc4)cc32)cc1] | 6-[2-(4-Chloro-phenyl)-2H-pyrazol-3-yl]-1-(4-methoxy-phenyl)-1H-benzoimidazole | 0.056 |
| 26 | 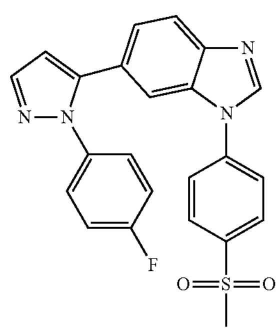 | 6-[2-(4-Fluoro-phenyl)-2H-pyrazol-3-yl]-1-(4-methanesulfonyl-phenyl)-1H-benzoimidazole | 0.28 |
| 27 | 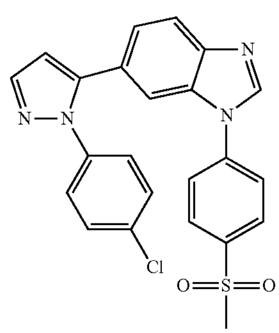 [SMILES: CS(=O)(=O)c1ccc(-n2cnc3ccc(-c4ccnn4-c4ccc(Cl)cc4)cc32)cc1] | 6-[2-(4-Chloro-phenyl)-2H-pyrazol-3-yl]-1-(4-methanesulfonyl-phenyl)-1H-benzoimidazole | 0.16 |
| 28 | 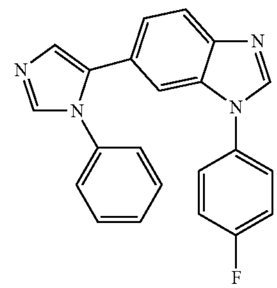 [SMILES: Fc1ccc(-n2cnc3ccc(-c4cncn4-c4ccccc4)cc32)cc1] | 1-(4-Fluoro-phenyl)-6-(3-phenyl-3H-imidazol-4-yl)-1H-benzoimidazole | 0.07 |
| 29 | 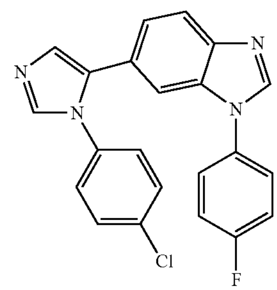 [SMILES: Fc1ccc(-n2cnc3ccc(-c4cncn4-c4ccc(Cl)cc4)cc32)cc1] | 6-[3-(4-Chloro-phenyl)-3H-imidazol-4-yl]-1-(4-fluoro-phenyl)-1H-benzoimidazole | 0.074 |
| 30 | 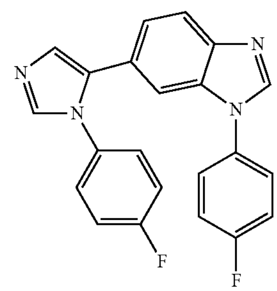 [SMILES: Fc1ccc(-n2cncc2-c2ccc3ncn(-c4ccc(F)cc4)c3c2)cc1] | 1-(4-Fluoro-phenyl)-6-[3-(4-fluoro-phenyl)-3H-imidazole-4-yl]-1H-benzoimidazole | 0.11 |

INTERMEDIATES

Intermediate A:
1-(4-Fluorophenyl)-1H-pyrazol-5-ylboronic acid

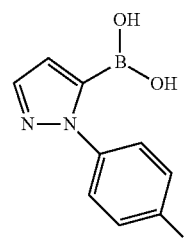

To a stirred solution of commercially available 1-(4-fluorophenyl)-1H-pyrazole [CAS No 81329-32-0] (1.6 g, 9.87 mmol) in THF (39.5 ml) was added drop wise at −78° C. under nitrogen atmosphere N-butyllithium (1.6 N in hexane, 6.47 ml, 10.4 mmol). After the mixture was allowed to stir at −78° C. for 1 h triisopropyl borate (7.65 g, 9.35 ml, 39.5 mmol) was added at −78° C. The mixture was allowed to stir at −78° C. for 1 h, gradually warmed to room temperature, and the pH of the mixture was adjusted to 5 with 1 M HCl solution. The mixture was evaporated and the remaining water layer extracted with ethyl acetate (2×30 ml). The combined organic layers were washed with brine (30 ml), dried over MgSO$_4$ and evaporated. The raw product was purified by column chromatography on silica gel (dichloromethane/ MeOH) and trituration (diethyl ether/hexane) to yield the title compound as a white solid (479 mg, 24%), MS (ISN) m/z=205.0 [(M−H)$^-$], mp 115° C.

Intermediate B: 1-(p-Tolyl)-1H-pyrazol-5-ylboronic acid

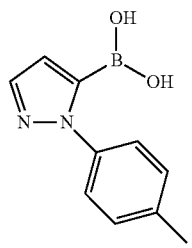

The title compound, off-white solid (629 mg, 37%), MS (ISN) m/z=201.2 [(M−H)$^-$], mp 111° C., was prepared in accordance with the general method of intermediate A from commercially available 1-(p-tolyl)-1H-pyrazole [CAS No. 20518-17-6] (1.35 g, 8.53 mmol) and triisopropyl borate.

Intermediate C: 1-(4-(Trifluoromethyl)-phenyl)-1H-pyrazol-5-ylboronic acid

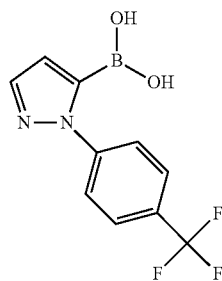 [SMILES: OB(O)c1ccnn1-c1ccc(C(F)(F)F)cc1]

The title compound, light brown solid (2.26 g, 62%), MS (ISN) m/z=255.5 [(M−H)$^-$], mp 306° C., was prepared in accordance with the general method of intermediate A from commercially available 1-(4-(trifluoromethyl)-phenyl)-1H-pyrazol [CAS No. 207797-05-5] (3 g, 14.1 mmol) and triisopropyl borate.

Intermediate D: 1-(4-Chlorophenyl)-1H-pyrazol-5-ylboronic acid

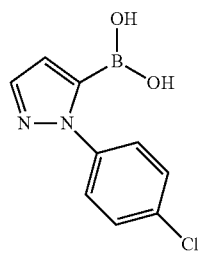 [SMILES: OB(O)c1ccnn1-c1ccc(Cl)cc1]

The title compound, light brown solid (400 mg, 17%), MS (ISN) m/z=221.2 [(M−H)$^-$], was prepared in accordance with the general method of intermediate A from commercially available 1-(4-chlorophenyl)-1H-pyrazol [CAS No. 25419-86-7] (1.87 g, 10.5 mmol) and triisopropyl borate.

Intermediate E: 6-Bromo-1-phenyl-1H-benzo[d]imidazole

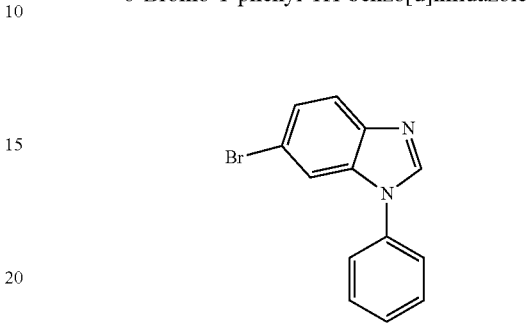

Step A

To a stirred mixture of commercially available 4-bromo-2-fluoro-1-nitrobenzene (1 g, 4.47 mmol) and potassium carbonate (680 mg, 4.92 mmol) in DMSO (17.9 ml) was added aniline (419 mg, 410 µl, 4.47 mmol) and the reaction mixture was allowed to stir for 65 h at room temperature. The reaction mixture was poured into water (100 ml) and extracted with ethyl acetate (2×70 ml). The combined organic layers were washed with water (1×50 ml), dried (MgSO$_4$) and evaporated. The crude product (orange solid, 1.32 g) was purified by flash chromatography on silica gel [heptane/ethyl acetate (0-10%)] to yield an orange solid (1.06 g, 3.62 mmol) which was subsequently dissolved in methanol (50.0 ml). To the stirred solution hydrochloric acid (37%, 50 ml) and tin(II) chloride dihydrate (4.9 g, 21.7 mmol) were added at room temperature, and afterwards the reaction mixture was allowed to stir at 80° C. for 1 hr. The reaction mixture was evaporated, ice and 3N sodium hydroxide solution (50 ml) were added, and the mixture was extracted with ethyl acetate (2×100 ml). The combined organic layers were washed with brine (50 ml), dried (MgSO$_4$) and evaporated. The crude product (0.94 g) was purified by flash chromatography on silica gel (heptane/ ethyl acetate 4:1) to yield 4-bromo-N2-phenyl-benzene-1,2-diamine as a light brown solid (429 mg, 36%), MS (ISN) m/z=261.0 [(M−H)$^-$], mp 103° C.

Step B

To a stirred mixture of 4-bromo-N2-phenyl-benzene-1,2-diamine (step A) (420 mg, 1.6 mmol) and trimethyl orthoformiate (4.8 g, 5 ml, 45.2 mmol), formic acid (1.2 g, 1 ml, 26.1 mmol) was added at room temperature, and afterwards the reaction mixture was allowed to stir at for 2 h under reflux conditions. The reaction mixture was cooled to room temperature, evaporated and extracted with ethyl acetate (2×40 ml). The combined organic layers were washed with sat. sodium bicarbonate solution (20 ml) and brine (20 ml), dried (MgSO$_4$) and evaporated. The crude product (400 mg) was purified by flash chromatography on silica gel (heptane/ethyl acetate 3:2) to yield the title compound as an off-white solid (358 mg, 82%), MS (ISP) m/z=275.0 [(M+H)$^+$].

Intermediate F:
6-Bromo-1-p-tolyl-1H-benzo[d]imidazole

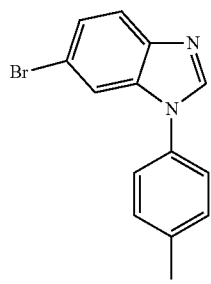 [SMILES: Cc1ccc(-n2cnc3ccc(Br)cc32)cc1]

Step A

4-Bromo-N2-p-tolyl-benzene-1,2-diamine, orange oil (0.95 g, 76%), MS (ISN) m/z=275.1 [(M−H)⁻], was prepared in accordance with the general method of intermediate E (step A) from commercially available 4-bromo-2-fluoro-1-nitrobenzene (1 g, 4.47 mmol) and p-toluidine (484 mg, 4.47 mmol).

Step B

The title compound, light brown oil (854 mg, 88%), MS (ISP) m/z=289.0 [(M+H)⁺], was prepared in accordance with the general method of intermediate E (step B) from 4-bromo-N2-p-tolyl-benzene-1,2-diamine (step A) (0.94 g, 3.39 mmol).

Intermediate G:
6-Bromo-1-(4-fluoro-phenyl)-1H-benzo[d]imidazole

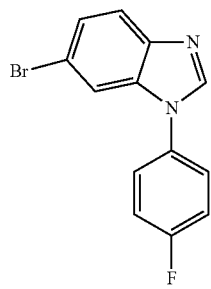 [SMILES: Fc1ccc(-n2cnc3ccc(Br)cc32)cc1]

Step A

4-Bromo-N2-(4-fluoro-phenyl)-benzene-1,2-diamine, brown oil (0.83 g, 33%), MS (ISN) m/z=281.1 [(M−H)⁻], was prepared in accordance with the general method of intermediate E (step A) from commercially available 4-bromo-2-fluoro-1-nitrobenzene (2 g, 8.94 mmol) and 4-fluoro-aniline (1.02 g, 8.94 mmol).

Step B

The title compound, off-white solid (751 mg, 88%), MS (ISP) m/z=293.0 [(M+H)⁺], mp 111.5° C., was prepared in accordance with the general method of intermediate E (step B) from 4-bromo-N2-(4-fluoro-phenyl)-benzene-1,2-diamine (step A) (0.82 g, 2.92 mmol).

Intermediate H:
6-Bromo-1-(4-chloro-phenyl)-1H-benzo[d]imidazole

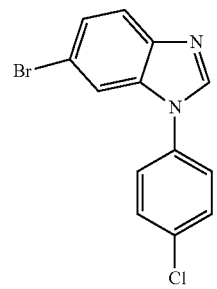 [SMILES: Clc1ccc(-n2cnc3ccc(Br)cc32)cc1]

Step A

4-Bromo-N2-(4-chloro-phenyl)-benzene-1,2-diamine, light brown oil (0.9 g, 41%), MS (ISP) m/z=299.3 [(M+H)⁺], was prepared in accordance with the general method of intermediate E (step A) from commercially available 4-bromo-2-fluoro-1-nitrobenzene (1.5 g, 6.71 mmol) and 4-chloro-aniline (0.97 g, 7.38 mmol).

Step B

The title compound, light brown solid (492 mg, 53%), MS (ISP) m/z=309.3 [(M+H)⁺], mp 131° C., was prepared in accordance with the general method of intermediate E (step B) from 4-bromo-N2-(4-chloro-phenyl)-benzene-1,2-diamine (step A) (0.9 g, 3.02 mmol).

Intermediate I: 6-Bromo-1-(4-trifluoromethyl-phenyl)-1H-benzo[d]imidazole

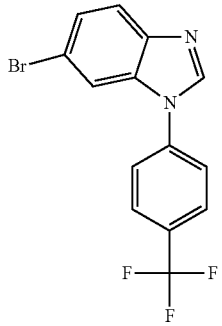 [SMILES: FC(F)(F)c1ccc(-n2cnc3ccc(Br)cc32)cc1]

Step A

4-Bromo-N2-(4-trifluoromethyl-phenyl)-benzene-1,2-diamine, light brown solid (0.46 g, 21%), MS (ISP) m/z=331.3 [(M+H)⁺], mp 84° C., was prepared in accordance with the general method of intermediate E (step A) from commercially available 4-bromo-2-fluoro-1-nitrobenzene (1.5 g, 6.71 mmol) and 4-trifluoromethyl-aniline (1.23 g, 7.38 mmol).

Step B

The title compound, light brown solid (461 mg, 97%), MS (ISP) m/z=341.3 [(M+H)⁺], mp 84.5° C., was prepared in accordance with the general method of intermediate E (step B) from 4-bromo-N2-(4-trifluoromethyl-phenyl)-benzene-1,2-diamine (step A) (0.46 g, 1.39 mmol).

Intermediate K: 6-Bromo-1-(2,4-difluoro-phenyl)-1H-benzo[d]imidazole

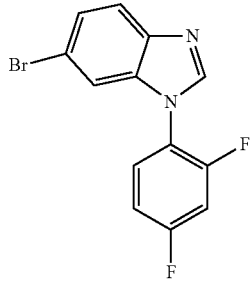 [SMILES: Fc1ccc(-n2cnc3ccc(Br)cc32)c(F)c1]

Step A

4-Bromo-N2-(2,4-difluoro-phenyl)-benzene-1,2-diamine, brown solid (1.98 g, 73%), MS (ISP) m/z=299.3 [(M+H)$^+$], mp 77° C., was prepared in accordance with the general method of intermediate E (step A) from commercially available 4-bromo-2-fluoro-1-nitrobenzene (2 g, 9.09 mmol) and 2,4-difluoro-aniline (2.35 g, 18.2 mmol).

Step B

The title compound, light brown solid (2.0 g, 98%), MS (ISP) m/z=309.3 [(M+H)$^+$], mp 84° C., was prepared in accordance with the general method of intermediate E (step B) from 4-bromo-N2-(2,4-difluoro-phenyl)-benzene-1,2-diamine (step A) (1.98 g, 6.62 mmol).

Intermediate L: 6-Bromo-1-pyridin-4-yl-1H-benzoimidazole

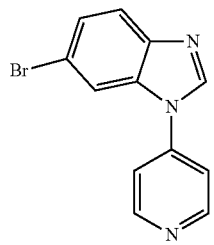 [SMILES: Brc1ccc2ncn(-c3ccncc3)c2c1]

Step A

4-Bromo-N2-pyridin-4-yl-benzene-1,2-diamine, white solid (0.31 g, 30%), MS (ISP) m/z=266.3 [(M+H)$^+$], mp 137.5° C., was prepared in accordance with the general method of intermediate E (step A) from commercially available 4-bromo-2-fluoro-1-nitrobenzene (0.865 g, 3.93 mmol) and 4-amino-pyridine (0.37 g, 3.93 mmol).

Step B

The title compound, white solid (207 mg, 67%), MS (ISP) m/z=274.3 [(M+H)$^+$], mp 132° C., was prepared in accordance with the general method of intermediate E (step B) from 4-bromo-N2-pyridin-4-yl-benzene-1,2-diamine (step A) (0.3 g, 1.14 mmol).

Intermediate M: 6-Bromo-1-(4-chloro-2-fluoro-phenyl)-1H-benzo[d]imidazole

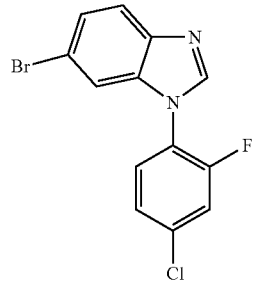 [SMILES: Fc1cc(Cl)ccc1-n1cnc2ccc(Br)cc21]

Step A

4-Bromo-N2-(4-chloro-2-fluoro-phenyl)-benzene-1,2-diamine, light brown oil (1.4 g, 49%), MS (ISP) m/z=317.3 [(M+H)$^+$], was prepared in accordance with the general method of intermediate E (step A) from commercially available 4-bromo-2-fluoro-1-nitrobenzene (2 g, 9.09 mmol) and 4-chloro-2-fluoro-aniline (2.65 g, 18.2 mmol).

Step B

The title compound, off-white solid (1.33 g, 92%), MS (ISP) m/z=327.3 [(M+H)$^+$], mp 154° C., was prepared in accordance with the general method of intermediate E (step B) from 4-bromo-N2-(4-chloro-2-fluoro-phenyl)-benzene-1, 2-diamine (step A) (1.4 g, 4.44 mmol).

Intermediate N: 6-Bromo-1-(4-methoxy-phenyl)-1H-benzo[d]imidazole

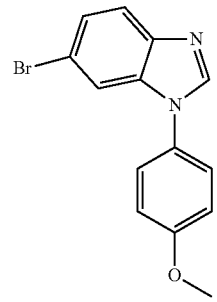 [SMILES: COc1ccc(-n2cnc3ccc(Br)cc32)cc1]

Step A

4-Bromo-N2-(4-methoxy-phenyl)-benzene-1,2-diamine, dark red solid (2.48 g, 93%), MS (ISP) m/z=293.4 [(M+H)$^+$], mp 96° C., was prepared in accordance with the general method of intermediate E (step A) from commercially available 4-bromo-2-fluoro-1-nitrobenzene (2.0 g, 9.09 mmol) and 4-methoxy-aniline (2.24 g, 18.2 mmol).

Step B

The title compound, light pink solid (2.3 g, 90%), MS (ISP) m/z=305.4 [(M+H)$^+$], mp 122° C., was prepared in accordance with the general method of intermediate E (step B) from 4-bromo-N2-(4-methoxy-phenyl)-benzene-1,2-diamine (step A) (2.47 g, 8.43 mmol).

Intermediate O: 6-Bromo-1-(4-methylsulfonyl-phenyl)-1H-benzo[d]imidazole

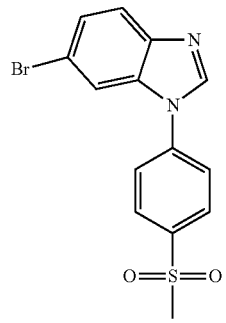

Step A

4-Bromo-N2-(4-methylsulfonyl-phenyl)-benzene-1,2-diamine, light brown solid (186 mg, 10%), MS (ISN) m/z=339.5 [(M−H)⁻], mp 179° C., was prepared in accordance with the general method of intermediate E (step A) from commercially available 4-bromo-2-fluoro-1-nitrobenzene (1.21 g, 5.49 mmol) and 4-methylsulfonyl-aniline (0.94 g, 5.49 mmol).

Step B

The title compound, off-white foam (147 mg, 79%), MS (ISP) m/z=353.3 [(M+H)⁺], was prepared in accordance with the general method of intermediate E (step B) from 4-bromo-N2-(4-methylsulfonyl-phenyl)-benzene-1,2-diamine (step A) (0.18 g, 0.53 mmol).

EXAMPLE 1

1-p-Tolyl-6-(2-p-tolyl-2H-pyrazol-3-yl)-1H-benzoimidazole

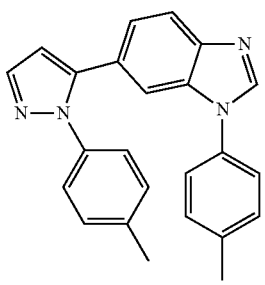

To a mixture of 6-bromo-1-p-tolyl-1H-benzo[d]imidazole (intermediate F) (100 mg, 348 μmol) and 1-p-tolyl-1H-pyrazol-5-ylboronic acid (intermediate B) (91.5 mg, 453 μmol) in 1,2-dimethoxyethane (3 ml) was added 2M sodium carbonate solution (696 μl, 1.39 mmol) and the reaction mixture was purged with argon for 10 min in an ultrasonic bath. To the stirred mixture tetrakis(triphenylphosphine)palladium(0) (80.5 mg, 69.6 μmol) was added at room temperature and the reaction mixture was allowed to stir under reflux conditions for 15 h. The reaction mixture was cooled to room temperature, poured into water (20 ml) and extracted with ethyl acetate (2×20 ml). The combined organic layers were washed with brine (1×20 ml), dried (MgSO₄) and evaporated. The crude material (200 mg) was purified by flash chromatography on silica gel (heptane/ethyl acetate 1:1) and trituration from diethyl ether/heptane to yield the title compound as a off-white solid (55 mg, 43%), MS (ISP) m/z=365.2 [(M+H)⁺], mp 165° C.

EXAMPLE 2

1-Phenyl-6-(2-phenyl-2H-pyrazol-3-yl)-1H-benzoimidazole

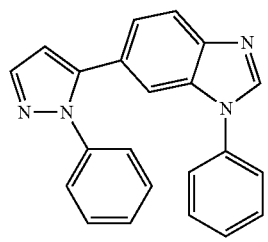 [SMILES: c1ccc(-n2nccc2-c2ccc3ncn(-c4ccccc4)c3c2)cc1]

The title compound, off-white solid (36 mg, 29%), MS (ISP) m/z=337.3 [(M+H)⁺], mp 194° C., was prepared in accordance with the general method of example 1 from 6-bromo-1-phenyl-1H-benzo[d]imidazole (intermediate E) (100 mg, 366 μmol) and commercially available 1-phenyl-1H-pyrazol-5-ylboronic acid [CAS No. 1238702-56-1] (89.5 mg, 476 μmol).

EXAMPLE 3

6-[2-(4-Fluoro-phenyl)-2H-pyrazol-3-yl]-1-phenyl-1H-benzoimidazole

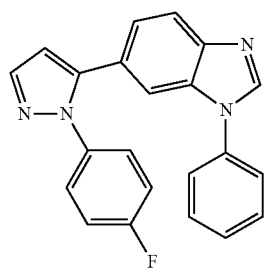

The title compound, off-white solid (39 mg, 30%), MS (ISP) m/z=355.2 [(M+H)⁺], mp 201° C., was prepared in accordance with the general method of example 1 from 6-bromo-1-phenyl-1H-benzo[d]imidazole (intermediate E) (100 mg, 366 μmol) and 1-(4-fluoro-phenyl)-1H-pyrazol-5-ylboronic acid (intermediate A) (98.0 mg, 476 μmol).

EXAMPLE 4

1-Phenyl-6-(2-p-tolyl-2H-pyrazol-3-yl)-1H-benzoimidazole

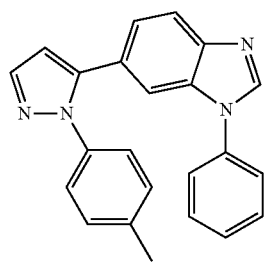 [SMILES: Cc1ccc(-n2nccc2-c2ccc3ncn(-c4ccccc4)c3c2)cc1]

The title compound, off-white foam (36 mg, 28%), MS (ISP) m/z=351.3 [(M+H)⁺], was prepared in accordance with the general method of example 1 from 6-bromo-1-phenyl-1H-benzo[d]imidazole (intermediate E) (100 mg, 366 µmol) and 1-p-tolyl-1H-pyrazol-5-ylboronic acid (intermediate B) (96.2 mg, 476 µmol).

EXAMPLE 5

6-(2-Phenyl-2H-pyrazol-3-yl)-1-p-tolyl-1H-benzoimidazole

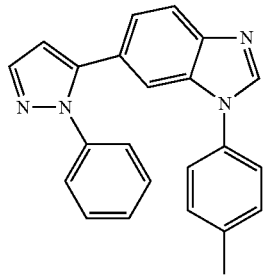 [SMILES: Cc1ccc(-n2cnc3ccc(-c4ccnn4-c4ccccc4)cc32)cc1]

The title compound, off-white solid (27 mg, 22%), MS (ISP) m/z=351.3 [(M+H)⁺], mp 146° C., was prepared in accordance with the general method of example 1 from 6-bromo-1-p-tolyl-1H-benzo[d]imidazole (intermediate F) (100 mg, 348 µmol) and commercially available 1-phenyl-1H-pyrazol-5-ylboronic acid [CAS No. 1238702-56-1] (85.1 mg, 453 µmol).

EXAMPLE 6

6-[2-(4-Fluoro-phenyl)-2H-pyrazol-3-yl]-1-p-tolyl-1H-benzoimidazole

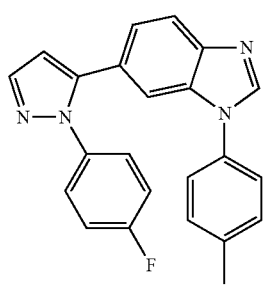

The title compound, off-white solid (22 mg, 17%), MS (ISP) m/z=369.2 [(M+H)⁺], mp 149° C., was prepared in accordance with the general method of example 1 from 6-bromo-1-p-tolyl-1H-benzo[d]imidazole (intermediate F) (100 mg, 348 µmol) and 1-(4-fluoro-phenyl)-1H-pyrazol-5-ylboronic acid (intermediate A) (93.3 mg, 453 µmol).

EXAMPLE 7

1-(4-Fluoro-phenyl)-6-(2-phenyl-2H-pyrazol-3-yl)-1H-benzoimidazole

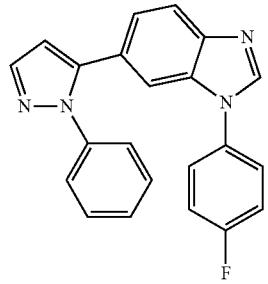 [SMILES: Fc1ccc(-n2cnc3ccc(-c4ccnn4-c4ccccc4)cc32)cc1]

The title compound, light brown solid (26 mg, 21%), MS (ISP) m/z=355.2 [(M+H)⁺], mp 194° C., was prepared in accordance with the general method of example 1 from 6-bromo-1-(4-fluoro-phenyl)-1H-benzo[d]imidazole (intermediate G) (100 mg, 344 µmol) and commercially available 1-phenyl-1H-pyrazol-5-ylboronic acid [CAS No. 1238702-56-1] (83.9 mg, 447 µmol).

EXAMPLE 8

1-(4-Fluoro-phenyl)-6-[2-(4-fluoro-phenyl)-2H-pyrazol-3-yl]-1H-benzoimidazole

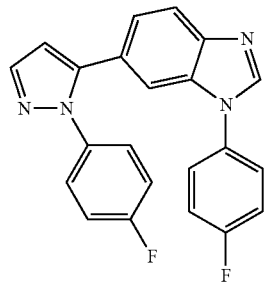

The title compound, white solid (40 mg, 31%), MS (ISP) m/z=373.1 [(M+H)⁺], mp 173° C., was prepared in accordance with the general method of example 1 from 6-bromo-1-(4-fluoro-phenyl)-1H-benzo[d]imidazole (intermediate G) (100 mg, 344 µmol) and 1-(4-fluoro-phenyl)-1H-pyrazol-5-ylboronic acid (intermediate A) (92.0 mg, 447 µmol).

EXAMPLE 9

1-(4-Fluoro-phenyl)-6-(2-p-tolyl-2H-pyrazol-3-yl)-1H-benzoimidazole

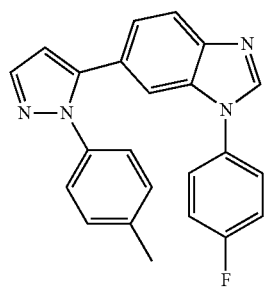

The title compound, light brown foam (78 mg, 61%), MS (ISP) m/z=369.2 [(M+H)⁺], was prepared in accordance with the general method of example 1 from 6-bromo-1-(4-fluoro-phenyl)-1H-benzo[d]imidazole (intermediate G) (100 mg, 344 µmol) and 1-p-tolyl-1H-pyrazol-5-ylboronic acid (intermediate B) (90.2 mg, 447 µmol).

EXAMPLE 10

1-(4-Fluoro-phenyl)-6-[2-(4-trifluoromethyl-phenyl)-2H-pyrazol-3-yl]-1H-benzoimidazole

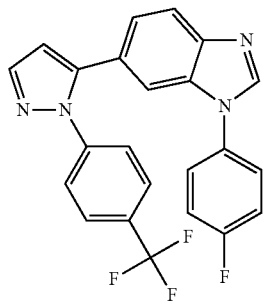

The title compound, yellow solid (45 mg, 31%), MS (ISP) m/z=423.5 [(M+H)⁺], mp 167° C., was prepared in accordance with the general method of example 1 from 6-bromo-1-(4-fluoro-phenyl)-1H-benzo[d]imidazole (intermediate G) (100 mg, 344 µmol) and 1-(4-trifluoromethyl-phenyl)-1H-pyrazol-5-ylboronic acid (intermediate C) (96.7 mg, 378 µmol).

EXAMPLE 11

6-[2-(4-Chloro-phenyl)-2H-pyrazol-3-yl]-1-(4-fluoro-phenyl)-1H-benzoimidazole

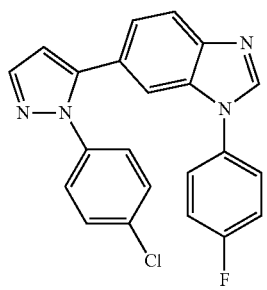

The title compound, off-white solid (28 mg, 21%), MS (ISP) m/z=389.4 [(M+H)⁺], mp 180° C., was prepared in accordance with the general method of example 1 from 6-bromo-1-(4-fluoro-phenyl)-1H-benzo[d]imidazole (intermediate G) (100 mg, 344 µmol) and 1-(4-chloro-phenyl)-1H-pyrazol-5-ylboronic acid (intermediate D) (84.0 mg, 378 µmol).

EXAMPLE 12

1-(4-Chloro-phenyl)-6-[2-(4-trifluoromethyl-phenyl)-2H-pyrazol-3-yl]-1H-benzoimidazole

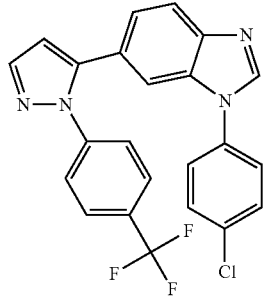

The title compound, light brown solid (56 mg, 39%), MS (ISP) m/z=439.4 [(M+H)⁺], mp 198° C., was prepared in accordance with the general method of example 1 from 6-bromo-1-(4-chloro-phenyl)-1H-benzo[d]imidazole (intermediate H) (100 mg, 325 µmol) and 1-(4-trifluoromethyl-phenyl)-1H-pyrazol-5-ylboronic acid (intermediate C) (91.6 mg, 358 µmol).

EXAMPLE 13

1-(4-Chloro-phenyl)-6-[2-(4-chloro-phenyl)-2H-pyrazol-3-yl]-1H-benzoimidazole

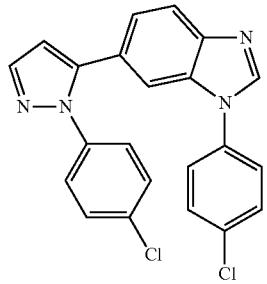

The title compound, light brown solid (29 mg, 22%), MS (ISP) m/z=405.4 [(M+H)⁺], mp 182° C., was prepared in accordance with the general method of example 1 from 6-bromo-1-(4-chloro-phenyl)-1H-benzo[d]imidazole (intermediate H) (100 mg, 325 µmol) and 1-(4-chloro-phenyl)-1H-pyrazol-5-ylboronic acid (intermediate D) (79.6 mg, 358 µmol).

EXAMPLE 14

6-[2-(4-Chloro-phenyl)-2H-pyrazol-3-yl]-1-(4-trifluoromethyl-phenyl)-1H-benzoimidazole

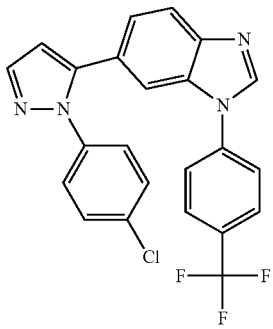

The title compound, light brown solid (37 mg, 29%), MS (ISP) m/z=439.4 [(M+H)+], mp 196° C., was prepared in accordance with the general method of example 1 from 6-bromo-1-(4-trifluoromethyl-phenyl)-1H-benzo[d]imidazole (intermediate I) (100 mg, 293 µmol) and 1-(4-chlorophenyl)-1H-pyrazol-5-ylboronic acid (intermediate D) (71.7 mg, 322 µmol).

EXAMPLE 15

1-(2,4-Difluoro-phenyl)-6-[2-(4-trifluoromethyl-phenyl)-2H-pyrazol-3-yl]-1H-benzoimidazole

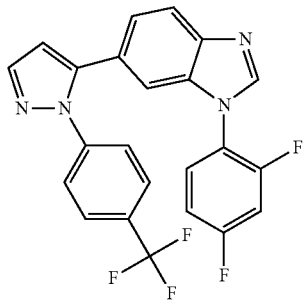 [SMILES: Fc1ccc(-n2cnc3ccc(-c4ccnn4-c4ccc(C(F)(F)F)cc4)cc32)c(F)c1]

The title compound, off-white solid (48 mg, 34%), MS (ISP) m/z=441.4 [(M+H)+], mp 129° C., was prepared in accordance with the general method of example 1 from 6-bromo-1-(2,4-difluoro-phenyl)-1H-benzo[d]imidazole (intermediate K) (100 mg, 324 µmol) and 1-(4-trifluoromethyl-phenyl)-1H-pyrazol-5-ylboronic acid (intermediate C) (91.1 mg, 356 µmol).

EXAMPLE 16

6-[2-(4-Chloro-phenyl)-2H-pyrazol-3-yl]-1-(2,4-difluoro-phenyl)-1H-benzoimidazole

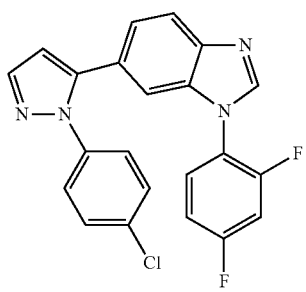

The title compound, off-white solid (29 mg, 22%), MS (ISP) m/z=407.4 [(M+H)+], mp 133° C., was prepared in accordance with the general method of example 1 from 6-bromo-1-(2,4-difluoro-phenyl)-1H-benzo[d]imidazole (intermediate K) (100 mg, 324 µmol) and 1-(4-chloro-phenyl)-1H-pyrazol-5-ylboronic acid (intermediate D) (79.2 mg, 356 µmol).

EXAMPLE 17

1-(2,4-Difluoro-phenyl)-6-[2-(4-fluoro-phenyl)-2H-pyrazol-3-yl]-1H-benzoimidazole

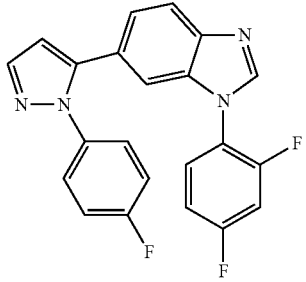 [SMILES: Fc1ccc(-n2nccc2-c2ccc3ncn(-c4ccc(F)cc4F)c3c2)cc1]

The title compound, light brown solid (69 mg, 55%), MS (ISP) m/z=391.5 [(M+H)+], mp 152° C., was prepared in accordance with the general method of example 1 from 6-bromo-1-(2,4-difluoro-phenyl)-1H-benzo[d]imidazole (intermediate K) (100 mg, 324 µmol) and 1-(4-fluoro-phenyl)-1H-pyrazol-5-ylboronic acid (intermediate A) (79.9 mg, 388 µmol).

EXAMPLE 18

6-[2-(4-Fluoro-phenyl)-2H-pyrazol-3-yl]-1-(4-trifluoromethyl-phenyl)-1H-benzoimidazole

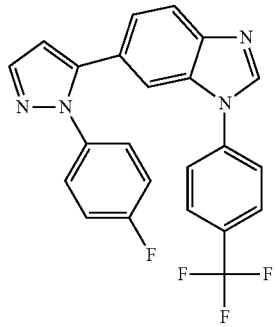 [SMILES: Fc1ccc(-n2nccc2-c2ccc3ncn(-c4ccc(C(F)(F)F)cc4)c3c2)cc1]

The title compound, light brown solid (67 mg, 54%), MS (ISP) m/z=423.3 [(M+H)+], mp 204° C., was prepared in accordance with the general method of example 1 from 6-bromo-1-(4-trifluoromethyl-phenyl)-1H-benzo[d]imidazole (intermediate I) (100 mg, 293 µmol) and 1-(4-fluoro-phenyl)-1H-pyrazol-5-ylboronic acid (intermediate A) (72.5 mg, 352 µmol).

EXAMPLE 19

1-(4-Chloro-phenyl)-6-[2-(4-fluoro-phenyl)-2H-pyrazol-3-yl]-1H-benzoimidazole

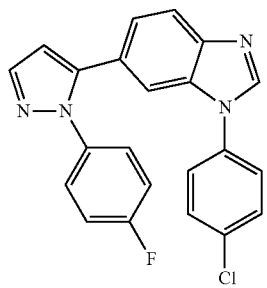

The title compound, off-white solid (44 mg, 35%), MS (ISP) m/z=389.4 [(M+H)⁺], mp 173° C., was prepared in accordance with the general method of example 1 from 6-bromo-1-(4-chloro-phenyl)-1H-benzo[d]imidazole (intermediate H) (100 mg, 325 µmol) and 1-(4-fluoro-phenyl)-1H-pyrazol-5-ylboronic acid (intermediate A) (80.3 mg, 390 µmol).

EXAMPLE 20

6-[2-(4-Fluoro-phenyl)-2H-pyrazol-3-yl]-1-pyridin-4-yl-1H-benzoimidazole

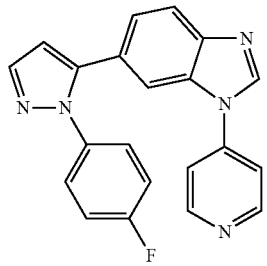

The title compound, off-white solid (62 mg, 48%), MS (ISP) m/z=356.4 [(M+H)⁺], mp 199° C., was prepared in accordance with the general method of example 1 from 6-bromo-1-pyridin-4-yl-1H-benzoimidazole (intermediate L) (100 mg, 365 µmol) and 1-(4-fluoro-phenyl)-1H-pyrazol-5-ylboronic acid (intermediate A) (90.2 mg, 438 µmol).

EXAMPLE 21

6-[2-(4-Chloro-phenyl)-2H-pyrazol-3-yl]-1-pyridin-4-yl-1H-benzoimidazole

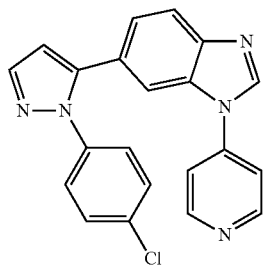

The title compound, white solid (50 mg, 37%), MS (ISP) m/z=372.4 [(M+H)⁺], mp 203° C., was prepared in accordance with the general method of example 1 from 6-bromo-1-pyridin-4-yl-1H-benzoimidazole (intermediate L) (100 mg, 365 µmol) and 1-(4-chloro-phenyl)-1H-pyrazol-5-ylboronic acid (intermediate D) (97.4 mg, 438 µmol).

EXAMPLE 22

1-(4-Chloro-2-fluoro-phenyl)-6-[2-(4-fluoro-phenyl)-2H-pyrazol-3-yl]-1H-benzoimidazole

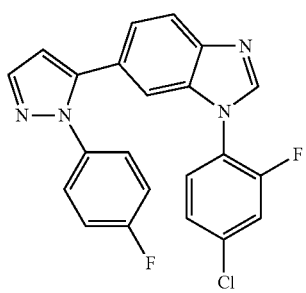

The title compound, white solid (46 mg, 37%), MS (ISP) m/z=407.5 [(M+H)⁺], mp 153° C., was prepared in accordance with the general method of example 1 from 6-bromo-1-(4-chloro-2-fluoro-phenyl)-1H-benzo[d]imidazole (intermediate M) (100 mg, 307 µmol) and 1-(4-fluoro-phenyl)-1H-pyrazol-5-ylboronic acid (intermediate A) (76.0 mg, 369 µmol).

EXAMPLE 23

1-(4-Chloro-2-fluoro-phenyl)-6-[2-(4-chloro-phenyl)-2H-pyrazol-3-yl]-1H-benzoimidazole

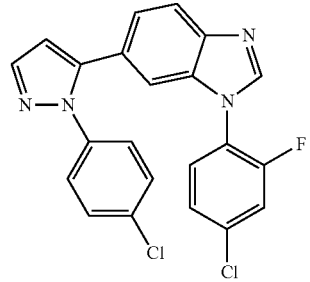 [SMILES: Fc1cc(Cl)ccc1-n1cnc2ccc(-c3ccnn3-c3ccc(Cl)cc3)cc21]

The title compound, white solid (23 mg, 18%), MS (ISP) m/z=423.4 [(M+H)⁺], mp 158° C., was prepared in accordance with the general method of example 1 from 6-bromo-1-(4-chloro-2-fluoro-phenyl)-1H-benzo[d]imidazole (intermediate M) (100 mg, 307 µmol) and 1-(4-chloro-phenyl)-1H-pyrazol-5-ylboronic acid (intermediate D) (82.1 mg, 369 µmol).

EXAMPLE 24

6-[2-(4-Fluoro-phenyl)-2H-pyrazol-3-yl]-1-(4-methoxy-phenyl)-1H-benzoimidazole

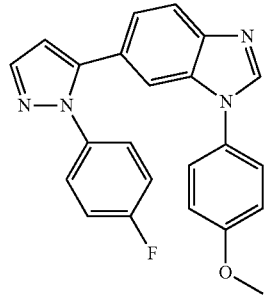

The title compound, off-white solid (34 mg, 27%), MS (ISP) m/z=385.5 [(M+H)⁺], mp 143° C., was prepared in accordance with the general method of example 1 from 6-bromo-1-(4-methoxy-phenyl)-1H-benzo[d]imidazole (intermediate N) (100 mg, 330 µmol) and 1-(4-fluoro-phenyl)-1H-pyrazol-5-ylboronic acid (intermediate A) (81.6 mg, 396 µmol).

EXAMPLE 25

6-[2-(4-Chloro-phenyl)-2H-pyrazol-3-yl]-1-(4-methoxy-phenyl)-1H-benzoimidazole

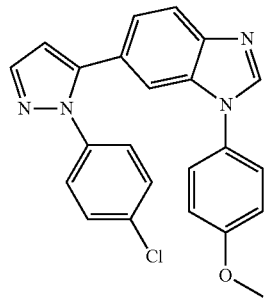

The title compound, off-white solid (16 mg, 12%), MS (ISP) m/z=401.5 [(M+H)⁺], mp 163° C., was prepared in accordance with the general method of example 1 from 6-bromo-1-(4-methoxy-phenyl)-1H-benzo[d]imidazole (intermediate N) (100 mg, 330 μmol) and 1-(4-chloro-phenyl)-1H-pyrazol-5-ylboronic acid (intermediate D) (88.1 mg, 396 μmol).

EXAMPLE 26

6-[2-(4-Fluoro-phenyl)-2H-pyrazol-3-yl]-1-(4-methanesulfonyl-phenyl)-1H-benzoimidazole

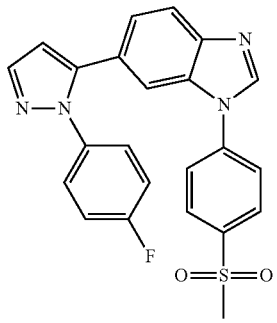

The title compound, white solid (12 mg, 14%), MS (ISP) m/z=433.4 [(M+H)⁺], mp 247° C., was prepared in accordance with the general method of example 1 from 6-bromo-1-(4-methylsulfonyl-phenyl)-1H-benzo[d]imidazole (intermediate O) (70 mg, 199 μmol) and 1-(4-fluoro-phenyl)-1H-pyrazol-5-ylboronic acid (intermediate A) (49.2 mg, 239 μmol).

EXAMPLE 27

6-[2-(4-Chloro-phenyl)-2H-pyrazol-3-yl]-1-(4-methanesulfonyl-phenyl)-1H-benzoimidazole

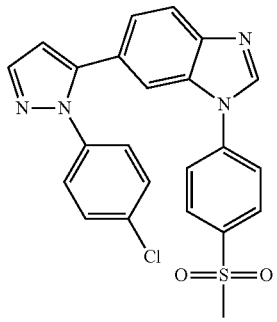

The title compound, white solid (13 mg, 15%), MS (ISP) m/z=449.4 [(M+H)⁺], mp 280° C., was prepared in accordance with the general method of example 1 from 6-bromo-1-(4-methylsulfonyl-phenyl)-1H-benzo[d]imidazole (intermediate O) (70 mg, 199 μmol) and 1-(4-chloro-phenyl)-1H-pyrazol-5-ylboronic acid (intermediate D) (53.2 mg, 239 μmol).

EXAMPLE 28

1-(4-Fluoro-phenyl)-6-(3-phenyl-3H-imidazol-4-yl)-1H-benzoimidazole

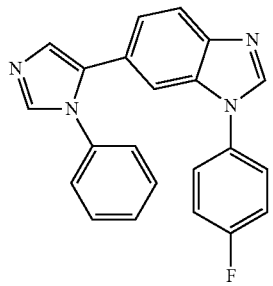 [SMILES: Fc1ccc(-n2cnc3ccc(-c4cncn4-c4ccccc4)cc32)cc1]

To a flame-dried reaction flask were added commercially available 1-phenyl-1H-imidazole (50.5 mg, 0.35 mmol), palladium(II)acetate (7.86 mg, 35.0 μmol), cesium fluoride (106 mg, 0.7 mmol), triphenylarsine (21.4 mg, 70.0 μmol) and 6-bromo-1-(4-fluoro-phenyl)-1H-benzo[d]imidazole (intermediate G) (204 mg, 0.7 mmol). The reaction flask was evacuated, and backfilled with argon, and this sequence was repeated twice. Afterwards DMF (1.75 ml) was added successively under a stream of argon by syringe at room temperature. The resulting mixture was allowed to stir at 140° C. under an argon atmosphere for 48 h. Afterwards the reaction mixture was cooled to room temperature, poured into water (20 ml), extracted with ethyl acetate (2×30 ml) and washed with brine (20 ml). The combined organic layers were dried (MgSO₄) and evaporated. The crude product was purified by flash chromatography on silica gel [dichloromethane/MeOH (0-3%)] and crystallization from dichloromethane/hexane to yield the title compound as an off-white solid (23 mg, 19%), MS (ISP) m/z=355.1 [(M+H)⁺], mp 216° C.

EXAMPLE 29

6-[3-(4-Chloro-phenyl)-3H-imidazol-4-yl]-1-(4-fluoro-phenyl)-1H-benzoimidazole

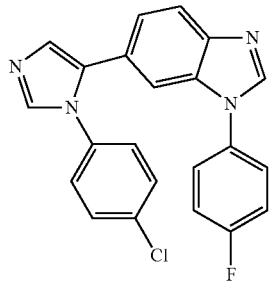

The title compound, off-white solid (20 mg, 15%), MS (ISP) m/z=389.5 [(M+H)⁺], mp 254° C., was prepared in accordance with the general method of example 28 from 6-bromo-1-(4-fluoro-phenyl)-1H-benzo[d]imidazole (intermediate G) (204 mg, 0.7 mmol) and commercially available 1-(4-chloro-phenyl)-1H-imidazole (62.5 mg, 0.35 mmol).

EXAMPLE 30

1-(4-Fluoro-phenyl)-6-[3-(4-fluoro-phenyl)-3H-imidazol-4-yl]-1H-benzoimidazole

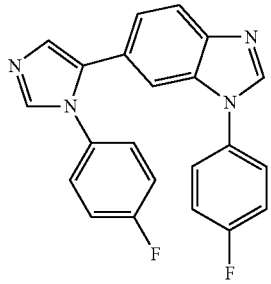

The title compound, light brown solid (26 mg, 20%), MS (ISP) m/z=373.5 [(M+H)$^+$], mp 247° C., was prepared in accordance with the general method of example 28 from 6-bromo-1-(4-fluoro-phenyl)-1H-benzo[d]imidazole (intermediate G) (204 mg, 0.7 mmol) and commercially available 1-(4-fluoro-phenyl)-1H-imidazole (56.8 mg, 0.35 mmol).

The invention claimed is:
1. A Compound of formula I

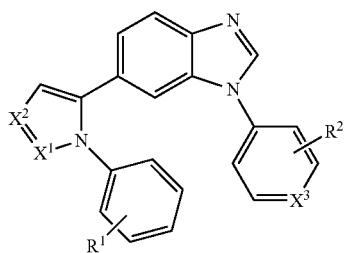

wherein
$R^1$ hydrogen, lower alkyl, halogen or lower alkyl substituted by halogen;
$R^2$ is hydrogen or halogen;
$X^1$ is N or CH;
$X^2$ is N or CH;
with the proviso that only one of $X^1$ or $X^2$ is N;
$X^3$ is C(R) or N;
and R is hydrogen, lower alkyl, halogen, lower alkyl substituted by halogen, lower alkoxy or SO$_2$-lower alkyl;
or a pharmaceutically acceptable acid addition salt, a racemic mixture or its corresponding enantiomer and/or optical isomers thereof.

2. A compound of formula IA according to claim 1,

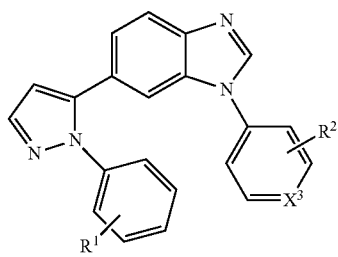

wherein
$R^1$ hydrogen, lower alkyl, halogen or lower alkyl substituted by halogen;
$R^2$ is hydrogen or halogen;
$X^3$ is C(R) or N;
and R is hydrogen, lower alkyl, halogen, lower alkyl substituted by halogen, lower alkoxy or SO$_2$-lower alkyl;
or a pharmaceutically acceptable acid addition salt, a racemic mixture or its corresponding enantiomer and/or optical isomers thereof.

3. The compound of formula IA according to claim 2, wherein the compound is
1-p-Tolyl-6-(2-p-tolyl-2H-pyrazol-3-yl)-1H-benzoimidazole
1-Phenyl-6-(2-phenyl-2H-pyrazol-3-yl)-1H-benzoimidazole
6-[2-(4-Fluoro-phenyl)-2H-pyrazol-3-yl]-1-phenyl-1H-benzoimidazole
1-Phenyl-6-(2-p-tolyl-2H-pyrazol-3-yl)-1H-benzoimidazole
6-(2-Phenyl-2H-pyrazol-3-yl)-1-p-tolyl-1H-benzoimidazole
6-[2-(4-Fluoro-phenyl)-2H-pyrazol-3-yl]-1-p-tolyl-1H-benzoimidazole
1-(4-Fluoro-phenyl)-6-(2-phenyl-2H-pyrazol-3-yl)-1H-benzoimidazole
1-(4-Fluoro-phenyl)-6-[2-(4-fluoro-phenyl)-2H-pyrazol-3-yl]-1H-benzoimidazole
1-(4-Fluoro-phenyl)-6-(2-p-tolyl-2H-pyrazol-3-yl)-1H-benzoimidazole
1-(4-Fluoro-phenyl)-6-[2-(4-trifluoromethyl-phenyl)-2H-pyrazol-3-yl]-1H-benzoimidazole
6-[2-(4-Chloro-phenyl)-2H-pyrazol-3-yl]-1-(4-fluoro-phenyl)-1H-benzoimidazole
1-(4-Chloro-phenyl)-6-[2-(4-trifluoromethyl-phenyl)-2H-pyrazol-3-yl]-1H-benzoimidazole
1-(4-Chloro-phenyl)-6-[2-(4-chloro-phenyl)-2H-pyrazol-3-yl]-1H-benzoimidazole
6-[2-(4-Chloro-phenyl)-2H-pyrazol-3-yl]-1-(4-trifluoromethyl-phenyl)-1H-benzoimidazole
1-(2,4-Difluoro-phenyl)-6-[2-(4-trifluoromethyl-phenyl)-2H-pyrazol-3-yl]-1H-benzoimidazole
6-[2-(4-Chloro-phenyl)-2H-pyrazol-3-yl]-1-(2,4-difluoro-phenyl)-1H-benzoimidazole
1-(2,4-Difluoro-phenyl)-6-[2-(4-fluoro-phenyl)-2H-pyrazol-3-yl]-1H-benzoimidazole
6-[2-(4-Fluoro-phenyl)-2H-pyrazol-3-yl]-1-(4-trifluoromethyl-phenyl)-1H-benzoimidazole
1-(4-Chloro-phenyl)-6-[2-(4-fluoro-phenyl)-2H-pyrazol-3-yl]-1H-benzoimidazole
6-[2-(4-Fluoro-phenyl)-2H-pyrazol-3-yl]-1-pyridin-4-yl-1H-benzoimidazole
6-[2-(4-Chloro-phenyl)-2H-pyrazol-3-yl]-1-pyridin-4-yl-1H-benzoimidazole
1-(4-Chloro-2-fluoro-phenyl)-6-[2-(4-fluoro-phenyl)-2H-pyrazol-3-yl]-1H-benzoimidazole
1-(4-Chloro-2-fluoro-phenyl)-6-[2-(4-chloro-phenyl)-2H-pyrazol-3-yl]-1H-benzoimidazole
6-[2-(4-Fluoro-phenyl)-2H-pyrazol-3-yl]-1-(4-methoxy-phenyl)-1H-benzoimidazole
6-[2-(4-Chloro-phenyl)-2H-pyrazol-3-yl]-1-(4-methoxy-phenyl)-1H-benzoimidazole
6-[2-(4-Fluoro-phenyl)-2H-pyrazol-3-yl]-1-(4-methanesulfonyl-phenyl)-1H-benzoimidazole or
6-[2-(4-Chloro-phenyl)-2H-pyrazol-3-yl]-1-(4-methanesulfonyl-phenyl)-1H-benzoimidazole.

4. A compound of formula IA-1 according to claim 1

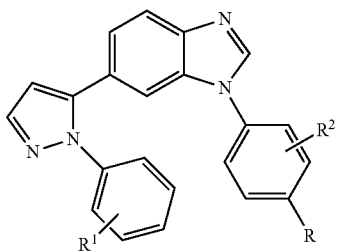

IA-1 wherein
- $R^1$ hydrogen, lower alkyl, halogen or lower alkyl substituted by halogen;
- $R^2$ is hydrogen or halogen;
- R is hydrogen, lower alkyl, halogen, lower alkyl substituted by halogen, lower alkoxy or $SO_2$-lower alkyl, or a pharmaceutically acceptable acid addition salt, a racemic mixture or its corresponding enantiomer and/or optical isomers thereof.

5. A compound of formula IA-1 according to claim 4 wherein the compound is
- 1-p-Tolyl-6-(2-p-tolyl-2H-pyrazol-3-yl)-1H-benzoimidazole
- 1-Phenyl-6-(2-phenyl-2H-pyrazol-3-yl)-1H-benzoimidazole
- 6-[2-(4-Fluoro-phenyl)-2H-pyrazol-3-yl]-1-phenyl-1H-benzoimidazole
- 1-Phenyl-6-(2-p-tolyl-2H-pyrazol-3-yl)-1H-benzoimidazole
- 6-(2-Phenyl-2H-pyrazol-3-yl)-1-p-tolyl-1H-benzoimidazole
- 6-[2-(4-Fluoro-phenyl)-2H-pyrazol-3-yl]-1-p-tolyl-1H-benzoimidazole
- 1-(4-Fluoro-phenyl)-6-(2-phenyl-2H-pyrazol-3-yl)-1H-benzoimidazole
- 1-(4-Fluoro-phenyl)-6-[2-(4-fluoro-phenyl)-2H-pyrazol-3-yl]-1H-benzoimidazole
- 1-(4-Fluoro-phenyl)-6-(2-p-tolyl-2H-pyrazol-3-yl)-1H-benzoimidazole
- 1-(4-Fluoro-phenyl)-6-[2-(4-trifluoromethyl-phenyl)-2H-pyrazol-3-yl]-1H-benzoimidazole
- 6-[2-(4-Chloro-phenyl)-2H-pyrazol-3-yl]-1-(4-fluoro-phenyl)-1H-benzoimidazole
- 1-(4-Chloro-phenyl)-6-[2-(4-trifluoromethyl-phenyl)-2H-pyrazol-3-yl]-1H-benzoimidazole
- 1-(4-Chloro-phenyl)-6-[2-(4-chloro-phenyl)-2H-pyrazol-3-yl]-1H-benzoimidazole
- 6-[2-(4-Chloro-phenyl)-2H-pyrazol-3-yl]-1-(4-trifluoromethyl-phenyl)-1H-benzoimidazole
- 1-(2,4-Difluoro-phenyl)-6-[2-(4-trifluoromethyl-phenyl)-2H-pyrazol-3-yl]-1H-benzoimidazole
- 6-[2-(4-Chloro-phenyl)-2H-pyrazol-3-yl]-1-(2,4-difluoro-phenyl)-1H-benzoimidazole
- 1-(2,4-Difluoro-phenyl)-6-[2-(4-fluoro-phenyl)-2H-pyrazol-3-yl]-1H-benzoimidazole
- 6-[2-(4-Fluoro-phenyl)-2H-pyrazol-3-yl]-1-(4-trifluoromethyl-phenyl)-1H-benzoimidazole
- 1-(4-Chloro-phenyl)-6-[2-(4-fluoro-phenyl)-2H-pyrazol-3-yl]-1H-benzoimidazole
- 1-(4-Chloro-2-fluoro-phenyl)-6-[2-(4-fluoro-phenyl)-2H-pyrazol-3-yl]-1H-benzoimidazole
- 1-(4-Chloro-2-fluoro-phenyl)-6-[2-(4-chloro-phenyl)-2H-pyrazol-3-yl]-1H-benzoimidazole
- 6-[2-(4-Fluoro-phenyl)-2H-pyrazol-3-yl]-1-(4-methoxy-phenyl)-1H-benzoimidazole
- 6-[2-(4-Chloro-phenyl)-2H-pyrazol-3-yl]-1-(4-methoxy-phenyl)-1H-benzoimidazole
- 6-[2-(4-Fluoro-phenyl)-2H-pyrazol-3-yl]-1-(4-methanesulfonyl-phenyl)-1H-benzoimidazole or
- 6-[2-(4-Chloro-phenyl)-2H-pyrazol-3-yl]-1-(4-methanesulfonyl-phenyl)-1H-benzoimidazole.

6. A compound of formula IA-2 according to claim 1

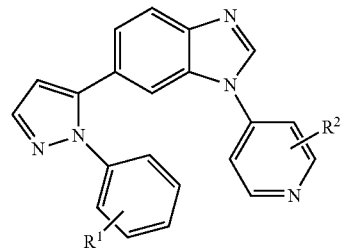

IA-2 wherein
- $R^1$ hydrogen, lower alkyl, halogen or lower alkyl substituted by halogen;
- $R^2$ is hydrogen or halogen;

or a pharmaceutically acceptable acid addition salt, a racemic mixture or its corresponding enantiomer and/or optical isomers thereof.

7. A compound of formula IA-2 according to claim 6, wherein the compounds are
- 6-[2-(4-Fluoro-phenyl)-2H-pyrazol-3-yl]-1-pyridin-4-yl-1H-benzoimidazole or
- 6-[2-(4-Chloro-phenyl)-2H-pyrazol-3-yl]-1-pyridin-4-yl-1H-benzoimidazole.

8. A compound of formula IB according to claim 1

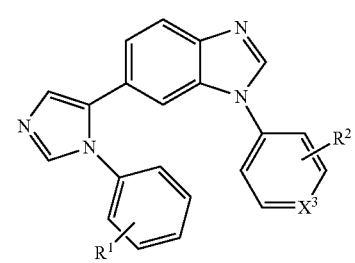

IB wherein
- $R^1$ hydrogen, lower alkyl, halogen or lower alkyl substituted by halogen;
- $R^2$ is hydrogen or halogen;
- $X^3$ is C(R) or N;
- and R is hydrogen, lower alkyl, halogen, lower alkyl substituted by halogen, lower alkoxy or $SO_2$-lower alkyl, or a pharmaceutically acceptable acid addition salt, a racemic mixture or its corresponding enantiomer and/or optical isomers thereof.

9. A compound according to claim 1, wherein the compound is
- 1-(4-Fluoro-phenyl)-6-(3-phenyl-3H-imidazol-4-yl)-1H-benzoimidazole
- 6-[3-(4-Chloro-phenyl)-3H-imidazol-4-yl]-1-(4-fluoro-phenyl)-1H-benzoimidazole or
- 1-(4-Fluoro-phenyl)-6-[3-(4-fluoro-phenyl)-3H-imidazol-4-yl]-1H-benzoimidazole.

10. A process for the manufacture of a compound of formula I as defined in claim 1, which process comprises reacting a compound of formula (1)

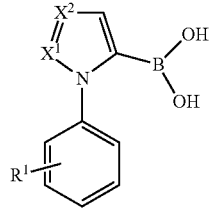

with a compound of formula (2)

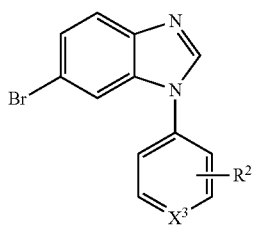

to afford a compound of formula (I)

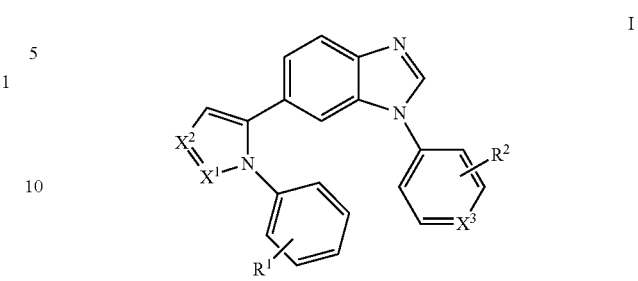

and optionally converting the compound obtained into a pharmaceutically acceptable acid addition salt.

11. A compound according to claim 1 when manufactured by a process according to claim 10.

12. A pharmaceutical composition comprising a compound according to claim 1 and a pharmaceutical acceptable carrier and/or adjuvant.

13. A method for the treatment of major depression, anxiety disorders, Parkinson's disease, Alzheimer's disease, amyotrophic lateral sclerosis, stroke, which method comprises administering a therapeutically effective amount of a compound as defined in claim 1 to a patient in need thereof.

* * * * *